US006887686B2

(12) United States Patent
Potter et al.

(10) Patent No.: US 6,887,686 B2
(45) Date of Patent: May 3, 2005

(54) **CLONING AND EXPRESSION OF *HAEMOPHILUS SOMNUS* TRANSFERRIN-BINDING PROTEINS**

(75) Inventors: Andrew A. Potter, Saskatoon (CA); Clement Rioux, Cap-Rouge (CA); Anthony B. Schryvers, Calgary (CA)

(73) Assignee: University of Saskatchewan, Saskatoon (CA)

( * ) Notice: Subject to any disclaimer, the term of this patent is extended or adjusted under 35 U.S.C. 154(b) by 311 days.

(21) Appl. No.: 10/098,808

(22) Filed: Mar. 13, 2002

(65) Prior Publication Data

US 2003/0007981 A1 Jan. 9, 2003

Related U.S. Application Data

(63) Continuation of application No. 09/405,728, filed on Sep. 24, 1999, now Pat. No. 6,391,316, which is a continuation-in-part of application No. 09/267,749, filed on Mar. 10, 1999, now abandoned.

(51) Int. Cl.[7] .................................................. C12P 21/06
(52) U.S. Cl. .................. 435/69.1; 435/320.1; 435/71.1; 435/252.3; 536/23.7; 536/24.1; 536/24.2; 536/24.32
(58) Field of Search .............................. 536/23.7, 24.1, 536/24.2, 24.32; 435/320.1, 69.1, 71.1, 252.3

(56) References Cited

U.S. PATENT DOCUMENTS

| 5,141,743 A | 8/1992 | Schryvers |
|---|---|---|
| 5,292,869 A | 3/1994 | Schryvers |
| 5,417,971 A | 5/1995 | Potter et al. |
| 5,521,072 A | 5/1996 | Potter et al. |
| 5,534,256 A | 7/1996 | Potter et al. |
| 5,708,149 A | 1/1998 | Loosmore et al. |
| 5,801,018 A | 9/1998 | Potter et al. |
| 5,876,725 A | 3/1999 | Potter et al. |
| 6,610,506 B1 * | 8/2003 | Lo et al. ..................... 435/69.1 |

FOREIGN PATENT DOCUMENTS

| EP | 0 586266 A1 | 3/1994 |
|---|---|---|
| WO | WO 90/12591 | 11/1990 |
| WO | WO 93/08283 | 4/1993 |
| WO | WO 93/21323 | 10/1993 |
| WO | WO 95/13370 | 5/1995 |
| WO | WO 95/33049 | 12/1995 |
| WO | 9720934 | * 6/1997 |

OTHER PUBLICATIONS

Archibald and Devoe, "Iron Acquisition by *Neisseria meningitidis* In Vitro," *Infection and Immunity* 27(2):322–334 (1980).
Archibald and DeVoe, "Removal of Iron From Human Transferrin by *Neisseria meningitidis*," *FEMS Microbiol. Lett.* 6:159–162 (1979).
Crosa, J.H., "Genetics and Molecular Biology of Siderophore–Mediated Iron Transport in Bavteria," *Microbiological Review* 53(4):517–530 (1989).
Gonzalez et al., "Identification and Characterization of a Porcine–Specific Transferrin Receptor in *Actinobacillus pleuropneumoniae*," *Molecular Microbiology* 4(7):1173–1179 (1990).
Herrington and Sparling, "*Haemophilus influenzae* Can Use Human Transferrin as a Sole Source for Required Iron," *Infection and Immunity* 48:248–251 (1985).
Ogunnariwo et al., "Response of *Haemophilus somnus* to Iron Limitation: Expression and Identification of a Bovine–Specific Transferrin Receptor," *Microbiol. Path.* 9:397–406 (1990).
Ogunnariwo et al., "Rapid Identification and Cloning of Bacterial Transferrin and Lactogerrin Receptor Protein Genes," *Journal of Bacteriology* 178(24):7326–7328 (1996) XP000915008.
Otto et al., "Transferrins and Heme–Compounds as Iron Sources for Pathogenic Bacteria," *Critical Reviews in Microbiol.* 18:217–233 (1992).
Schryvers, A.B., "Identification of the Transferrin–and Lactoferrin–Binding Proteins in *Haemophilus influenzae*," *J. Med. Microbiol.* 29:121–130 (1989).
Weinberg, Eugene D., "Iron and Infection," *Microbiological Reviews* 42(1):45–66 (1978).

* cited by examiner

Primary Examiner—Jennifer E. Graser
(74) Attorney, Agent, or Firm—Robins & Pasternak LLP

(57) ABSTRACT

Cloning and expression of genes encoding *H. somnus* transferrin-binding proteins are described. The transferrin-binding proteins can be used in vaccine compositions for the prevention and treatment of *H. somnus* infections, as well as in diagnostic methods for determining the presence of *H. somnus* infections.

20 Claims, 17 Drawing Sheets

Figure 2:
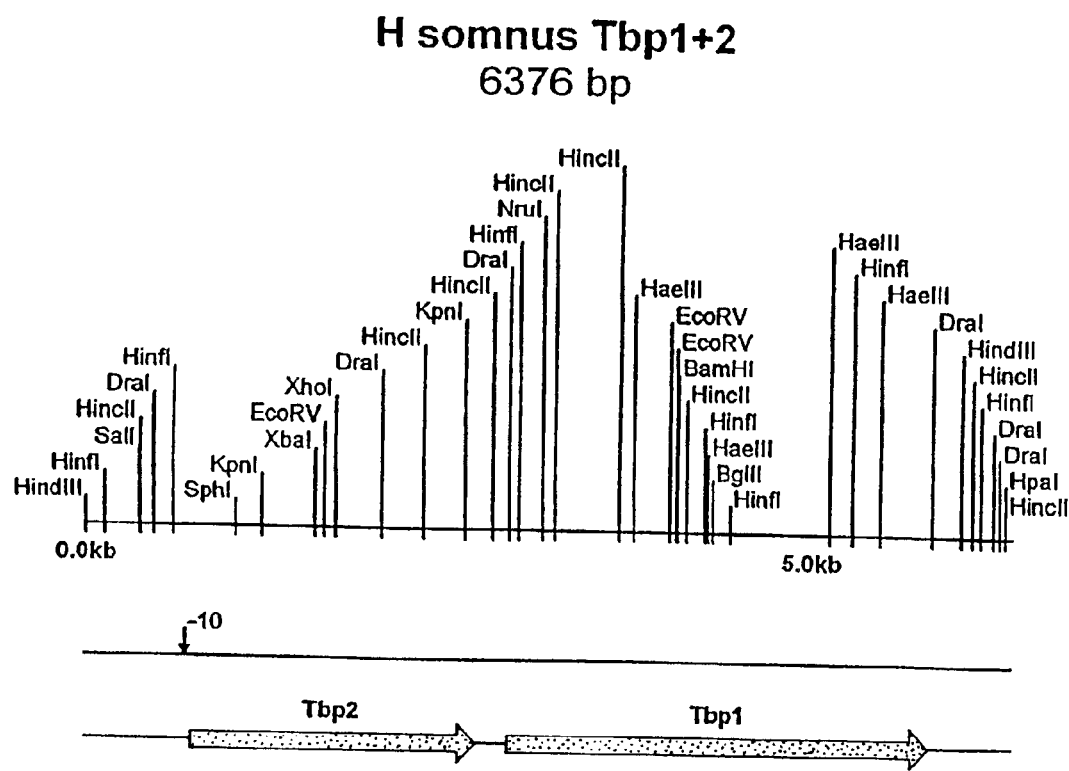

```
   1 aagcttgcat aattgcttca acgccttatc actataccgt aaagtgtaca tcactcaatt
  61 cctaacatct tgcatacctc tgcgtgagaa taactcattg gggttttgtt gtagtcttcc
 121 aaagactcac gatatactgc aaggtcatat tcatcttcga tttttttcaaa aacggcattc
 181 ctgaacagtt cggatagcgt aatattattt gttttttgcat aggacttaaa taattgctcg
 241 tcttgagcgt ttagtcttac tgaaatagcc atagtaaaat ttcctttcat tttgtattac
 301 attgtaatac atttatacag aatttgcaat ataggtgaaa aaagaaacag agattagacg
 361 tggtcgacac gttgttttta actgacacgt tcatttggtt ttcgtgacaa aatatcgcag
 421 agaagttttt acggcacgat tagataaaaa attaaattta aagagaaaat ctcgcaaggt
 481 aaaaaccgtc agctaacgtt gttggaaatg attgcccgcc ctcagatcga ccaaaatcgc
 541 acgtcttaat cgttccgagt gctgtatcgt tacaacaaac agcggctgtt taaggaatcc
 601 atcagcagcg tgggcgtgtt gaaaactgta tgcattcctt aaaaaaatac atataataat
 661 aatttttatt tgcatatttt atataatata agaaggata taggtaaatg acctctttca
 721 aattattagg cttttcggtc ttgagtgtgg ctttgctctc tgcctgctct tccggcaaag
 781 gtggctttga tttagacgac gtcgagcata ccccccccctc ctcctcgggt agttcccgcc
 841 ccacttatca agatgttccg actggacaac ggcagcaaga aatagtagaa gaaatcaact
 901 cacctgctct aggttatgcg acagaaattc cgcgtaggaa tatttcgcca atgcccacca
 961 cgggcacaaa agaaagtaat gctcgtgttg ccattactgc ccagcaagtt gcccctctta
1021 gcatgccttt taattcaata aaagaagatt ttatcaaaag gctaatagca gaaaacacca
1081 agaaaaatgc acgaggtaga gatgtaaaat attttgatga tacagatgac gtgttgtttg
1141 cacatgatgg atctaattta gcgcataaac gtgatttaca atatgttcga gttgggtatg
1201 tgttgggtac ccgaaagatt gaacttgttt tttcccatga taaaaaaaca agagatcaat
1261 ttcctgctgg tgggtaggt tatgttttt accaaggcac tagccctgcg gttacattac
1321 ctacacaaac cgtaacatac aaaggctatt gggattttgt tagtgatgcc ttcaatgaac
1381 gaactttagc tgaagatttt acacaggaaa atagttctgc tactagcaat ataccgggca
1441 atcaaatcgg tgcgacttca atggatgcat tggttaatcg caaagtttca ggagaaaaaa
1501 tcaatattgc tcacagtgct gagtttactg ctgattttgg cagtaaaaaa ctttcaggtg
1561 aattaaaaag taacggttat gtttctagaa tagaaaatga gcaacaagat gtaaaaacac
1621 gctacaaaat tgatgctgat atcaaaggca accgttttgt cggttcagca acagcacaag
1681 aaaaaagtca caccatcttc ggcaaggatg cggacaaacg tctcgagggc ggtttctttg
1741 gtcctaaagc cgaggaactg gcaggtaaat ttctgaccga tgataattcc ctgtttgtcg
1801 tctttggtgc aaaacgtgaa agtaaaggcg atgaaaaact agaaaccgc tttgatgccg
1861 ttaaaatcag cacggatagt aataaattag aaaaagaaac gatggatacg ttcggcaatg
1921 cggcgtattt agtgttggac ggcagacagt ttcctttggt gccggaaagt aatgccggta
1981 cgacgggcgc tggcaacaca ggcaagaatg agtttatcag caccatagac ggtagccatt
2041 taaacaaaac aaatcatgaa aaccacaaaa aatacaaagt taccgtatgt tgcagtaatt
2101 tggtgtatgt gaaattcggc agctatgggg aacaaacaac agcaaacgat gcttcaaaca
2161 gcactgccgg tgcagcaact acgcataaca gcacattaac aaacggacac ctttttcctaa
2221 caggtgaacg tacttcgctt actgatatgg cgaagcaaag tggtgcagca aagtatattg
2281 gcacatggca agccaacttt ttaagtagca aaggacaggt tggcagtgtt gacgccggtg
2341 atccgcgtaa cgatagtggt aaaagccgtg ctgaatttga tgttaatttt ggtggtaaga
2401 cagttacagg caagtttttt gatgccgacg gtattcaacc cgccctcaca atggatagta
2461 ccaagattga aggtaacggc ttctcgggta cagctaagac aactggtagt ttgcaattag
2521 ataaaggcag tacaggtgcg ggtataacag taaccttcac cgatgctaaa gtcgatggcg
2581 cattctacgg tccgaatgca gaagaaatcg gcggtaccat cacatcgaat ggcacgggcg
2641 ataaagtcgg tggggtgttc ggtgcgaaac gccaagaact atcgcaacag aaatgaaatc
2701 ttaactctag ctacctgaaa catatttcag gtagcaggat gggtatctgc tgatatgctc
2761 aacctgcttg aaaaagtttg tcaaatccgc cgcctgtcgt tgttgacggt gtgatgttgc
2821 agtggcaaat cgctcggctt tgttgagaaa gcatgaccca tccgtctttt actcacacgg
2881 aacgaaaaaa atgtctacaa aaccttgtt taaacttaag ctgataacat tggctgtcag
```

FIG. 1A

```
2941 cacgattttt ttaccttta ctgaggcggt tgccgatact gaatcaccga gtagcaatac
3001 agaagcagtg ctggagttag aagctatcca ggtgcaagcc aaacacgaga tcagcagaca
3061 tgacaatgaa gtcaccggtt tgggtaaggt ggtcaaaagc agtgaagaca ttgataaaga
3121 actgattttg aatattcgcg atttgacccg ttatgatccc ggtatttcgg tggtggagca
3181 gggacgtggt gcaacgtcag gctatgcaat gcgtggtgtt gacagaaacc gcgtggctat
3241 gttggtggac ggcttggac aggcgcagtc ctattctacc ttgaaatccg atgccaacgg
3301 cggggcgatt aatgaaattg aatatgagaa tattaaatca attgaattga gcaagggtc
3361 cagttcggca gaatacggta gcggtgcctt gggcggtgcg gtagggtttc gtaccaaaga
3421 agctgatgat gtgattaaag aggggcaaaa ctgggcttg aacagtaaaa cggcttacag
3481 cagcaaaaac agccagttta cccaatccgt tgccggtgcg ttccgtgtcg gcggttttga
3541 cagtttggcg atttttaccc atcgtaaagg taaggaaacc cgcgtgcatc ctgctgccga
3601 agaaatacaa catacttacc aaccattgga agggtatttt aatcggtatg aggttgacca
3661 aaaccgcaac ggaaagcctg ttctggcgaa tgcgtattat atacttgccg atgaatgctc
3721 taatctaagt gatccgagtt gtcgtcatgc caaggccaag acgaataggg tgggtgcccc
3781 ggagaacaat cctaattgga cgcccgaaga gcaggcacag gctgctaaaa tgccgtatcc
3841 gacacgtacc gcctctgcca aagattatac gggtcctgac cgcatcagcc ctaatccgat
3901 ggactaccaa agtcactctt tcttctggaa aggtggttac cgcttgtcgc ctaaccatta
3961 tgtcggcggg gtgttggaac atacgaagca gcgttacgat atccgtgata tgacgcaacg
4021 ggcgtattac acgaaagagg atatctgcca cagcggatcc agttgccaaa cgttggataa
4081 aaatgagacg gacaaggta atttcggtat cacgttgact gataatcctt tggacggttt
4141 ggtatatgat gccggcaatc aagctcgtgg cgtgcggtac ggacggggta aattttttaa
4201 tgaacgccat acgaaaaatc gctcgggtat cttttaccgc tatgagaatc ccgataaaaa
4261 ttcttggcca gatagcttga ccttgagtat tgaccgccaa gatctcaaac tgtcgagccg
4321 tatccattgg acgtattgca ccgattatcc tcatgtggca cgttgccgtg ccagcttgga
4381 caaaccttgg tctaattacc gtaccgagaa aaacgattat caagaacgac tcaatctggg
4441 acaattcaat tgggaaaaaa cttttaatct gggctttacc acgcataagg tgaatatcgc
4501 cgccggcttt ggtacacatc gctccaccct acaacatggc gacttatatg ctgaatatgt
4561 caccttgcca ccgtatacag aggaaaaagt gtatggcgaa gataataagg tcaaacaaaa
4621 tccgacagca gaagaaaaag agaaattaca atacggcaat ggttcttatg acaaacctcg
4681 cgtatataga cgtaaaaaca cgccggaatt aaaaactgtc aatgggtgca atgagacagc
4741 aggcgataac cgtgactgct cgccacgtgt gattacgggc agacagtatt accttgcctt
4801 gcgtaaccat attgcctttg gtgaatgggc agacttgggg ttgggcgtgc ggtacgacaa
4861 ccataccttc cgctcgaatg acccgtggac caaggtggc aactaccaca actggtcgtg
4921 gaatgcgggc gtgagcctca aaccaacccg ccactttgtc gtgtcttacc gtgtgtccag
4981 cggttttcgt gtccccgctt tttatgagct gtacggcgtg cgtacggggg cttctggtaa
5041 agacaatcca ctcacacaaa aagagttctt gagccgtaaa ccgttgaaaa gcgaaaaagc
5101 ctttaaccaa gaaattggtt tggccgttca gggcgatttt ggtgtgatag agaccagttt
5161 cttccaaaac aactataaaa acctgcttgc ccgtgcagat aaatatgtcg aggattggg
5221 ttatgtaacc gattttaca acacccaaga tgtcaaactc aacggtatca atatcttggg
5281 tagaatctac tgggaaggca tcagcgatag gctgcctgaa ggcttgtatt ccacacttgc
5341 ttacaaccgt atcaatatca aagcacgcaa attgcacgac aatttacca atgtgtctga
5401 gccgacattg gaagcagtgc aaccgggacg cattattgca agtatcggct atgatgaccc
5461 tgagggcaga tggggcctta atttaagcgg cacctactct caagccaaac aacgtgacga
5521 agtggtcggc gaaaaagtgt tcggcaaggg tggcagcatt aaacggacga tcaacagcaa
5581 acgcactcgt gcttggtata tttatgattt gacggcatac tacacttgga agaaaaatt
5641 cacgttgaga gccggtatct ataatttaac caatcgtaca tatagcacat gggaaagtgt
5701 gcgtcagtcc gctgccaatg cggtcaatca agacctaggt acacgttcgg cacgttttgc
5761 cgcacggggc agaaacttta ccgtgagtat ggaaatgaag ttttaattaa aaaactgtct
5821 gcaagctgtt taaaaaacag ttaagatgat ttgttcgtat aaatagctgc ctgaagtctt
5881 gttatgcagg ttcaggcagc ttgacattac aaaaaaagga aaaagtcta atggaagaca
5941 aatatgctat ttgtcggcaa cgaaaaattg ttgcaatgga ttagcagttc aagtggcttc
6001 cggtattttt tatcgcactt tttctatcta taagcttgaa atctttattt ccgaacttat
6061 attttcgctg tttgttaatt tcactattgg aaaaggaaat attatgtcaa caaatcaaga
6121 aacacgtggt tttcagtctg aagttaaaca gcttttacaa ttgatgattc attctcttta
6181 ttcaaataaa gagatttttt tgcgtgagtt gatttccaat gcgtctgatg cggcggataa
6241 attgcgtttt aaagccttgt ctgcacctga attatatgaa ggagatggtg atttaaaagt
6301 gcggatcagt tttgacgcag agaaggtac gttaaccatt agcgataatg gtattggtat
6361 gacgagagag caggtg
```

FIG. 1B

MSTKPLFKLKLITLAVSTIFLPFTEAVADTESPSSNTEAVLELEAIQVQAKHEISRHDNEVTGLGKVVKSSEDIDKELIL
NIRDLTRYDPGISVVEQRGATSGZAMRGVDNRRVAMLVDGLGQAQSYSTLKSDANGAINEIEYENIKSIELSKGSSSA
EYGSGALGGAVGFRTKEADDVIKEGQNWGLNSKTAYSSKNSQFTQSVAGAFRVGGFDSLAIFTHRKGKETRVHPAAEEIQ
HTYQPLEGYFNRYEVDQNRNGKPVLANAYYILADECSNLSDPSCRHAKAKTNRVGAPENNPNWTPEEQAQAAKMPYPTRT
ASAKDYTGPDRISPNPMDYQSHSFFWKGGYRLSPNHYVGGVLEHTKQRYDIRDMTQRAYYTKEDICHSGSSCQTLDKNET
DKGNFGITLTDNPLDGLVIDAGNQARGVRYGRGKFFNERHTKNRSGIFYRYENPDKNSWPDSLTLSIDRQDLKLSSRIHW
TYCTDYPHVARCRASLDKPWSNYRTEKNDYQERLNLGQFNWEKTFNLGFTTHKVNIAAGFGTHRSTLQHGDLYAEYVTLP
PYTEEKVYGEDNKVKQNPTAEEKEKLQYGNGSYDKPRVYRRKNTPELKTVNGCNETAGDNRDCSPRVITGROYYLALRNH
IAFGEWADIGLGVRYDNHTFRSNDPWTKGGNYHNWSWNAGVSLKPTRHFVVSYRVSSGFRVPAFYELYGVRTGASGKDNP
LTQKEFLSRKPLKSEKAFNQEIGLAVQGDFGVIETSFFQNNYKNLLARADKYVEGLGYVTDFYNTQDVKLNGINILGRIY
WEGISDRLPEGLYSTLAYNRINIKARKLHDNFINVSEPTLEAVQPGRIIASIGYDDPEGRWGLNLSGTYSQAKQRDEVVG
EKVFGKGGSIKRTINSKRTINSKRTAWYIYDLTAYYTWKEKFTLRAGIYNLTNRKYSTWESVRQSAANAVNQDLGTRSARFAARG
RNFTVSMEMKF

FIG. 3

MTSFKLLGFSVTLSVALLSACSSGKGGFDLDDVEHTPPSSSGSSRPTYQDVPTGQRQEIVEEINSPALGYATEIPRRNIS
PMPTTGTKESNARVAITAQQVAPLSMPFNSIKEDFIKRLIAENTKKNARGRDVKYFDDTDDVLFAHDGSNLAHKRDLQYV
RVGYVLGTRKIELVFSHDKKTRDQFPAGWVGYVFYQGTSPAVTLPTQTVTYKGYWDFVSDAFNERTLAEDFTQENSSATS
NIPGNQIGATSMDALVNRKVSGEKINIAHSAEFTADFGSKKLSGELKSNGYVSRIENEQQDVKTRYKIDADIKGNRFVGS
ATAQEKSHTIFGKDADKRLEGGFGPKAEELAGKFLTDDNSLFVVFGAKRESKGDEKLETRFDAVKISTDSNKLEKETMD
TFGNAAYLVLDGRQFPLVPESNAGTTGAGNTGKNEFISTIDGSHLNKTNHENHKKYIKVTVCCSNLVYVKFGSYGEQTTAN
DASNSTAGAATHNSTLTNGHLFLTGERTSLTDMAKQSGAAAKYIGTWQANFLSSKGQVGSVDAGDPRNDSGKSRAEFDVN
FGGKTVTGKFFDADGIQPALTMDSTKIEGNGFSGTAKTTGSLQLDKGSTGAGITVTFTDAKVDGAFYGPNAEEIGGTITS
NGTGDRVGGVFGAKRQELSQQK

FIG. 4

```
cgacgccagt gccaagcttg catgcctgca ggtgatctaa gcttcccggg atccaagagg    60
tgaagagatt tattggattg gaccaatagg actggcagaa atgaatcgg aaggaacgga   120
cttccatgcc gttaaaaacg gctatgtgtc aattacaccc attcaaacag atatgacggc   180
atatcattca atgacagctt tacaacaatg gttagataag gaataacgat aatcttttca   240
tcgaaggaat aaaacatgaa aattttcggt acgctatatg ataaaactat gcaatgggca   300
aatcaccgtt ttgctacatt ttggctaact tttgttagtt ttattgaggc tattttcttc   360
ccaataccac ctgatgtcat gcttattccg atgtcaataa ataaacctaa atgtgctact   420
aaatttgcat tttatgcagc aatggcttca gccattggtg gggcaattgg ttatggatta   480
ggttattacg cttttgattt catacaaagt tatattcaac aatggggtta tcaacaacat   540
tgggaaactg ctctttcttg gttcaaagaa tggggtattt gggtagtttt cgttgcaggt   600
ttttcaccta ttccttataa aattttttacg atttgtgcag gcgtcatgca aatggcattt   660
ttgcctttct tacttactgc ctttatttct cgtattgcaa gattttttgct cgttacccat   720
ttagcggctt ggagcggaaa aaaatttgct gcgaaattac gtcaatctat tgaatttatc   780
ggttggtcag ttgtcattat tgctatagtt gtatatcttg tcttgaaata atctaagata   840
aaaatgaat ataaagtaac ggagaattta c atg aaa aaa ttt tta cct tta       892
                                  Met Lys Lys Phe Leu Pro Leu
                                   1               5 tct att agt atc act gta cta gct gct tgt agt tca cac act ccg gct    940
Ser Ile Ser Ile Thr Val Leu Ala Ala Cys Ser Ser His Thr Pro Ala
         10              15              20 ccg gta gaa aat gct aag gat tta gca cca agt att atc aaa ccg att    988
Pro Val Glu Asn Ala Lys Asp Leu Ala Pro Ser Ile Ile Lys Pro Ile
     25              30              35 aat ggt aca aac tca acc gct tgg gaa cct caa gtt att caa caa aag   1036
Asn Gly Thr Asn Ser Thr Ala Trp Glu Pro Gln Val Ile Gln Gln Lys
 40              45              50              55 atg ccc gaa agt atg aga gtg ccg aaa gca aca aac tcc act tat caa   1084
Met Pro Glu Ser Met Arg Val Pro Lys Ala Thr Asn Ser Thr Tyr Gln
             60              65              70 cct gaa atc att caa caa aat caa caa aaa aca gaa tcg ata gca aaa   1132
Pro Glu Ile Ile Gln Gln Asn Gln Gln Lys Thr Glu Ser Ile Ala Lys
         75              80              85
```

FIG. 11A

```
aaa cag gct cta caa aat ttt gaa att cca aga gat cct aaa act aat    1180
Lys Gln Ala Leu Gln Asn Phe Glu Ile Pro Arg Asp Pro Lys Thr Asn
            90              95                  100 gtg cct gtt tat agc aaa att gat aag ggt ttt tac aaa ggt gat act    1228
Val Pro Val Tyr Ser Lys Ile Asp Lys Gly Phe Tyr Lys Gly Asp Thr
105             110                 115 tac aaa gta cgc aaa ggc gat acc atg ttt ctt att gct tat att tca    1276
Tyr Lys Val Arg Lys Gly Asp Thr Met Phe Leu Ile Ala Tyr Ile Ser
120             125                 130                 135 ggc atg gat ata aaa gaa ttg gcc aca cta aat aat atg tct gag cca    1324
Gly Met Asp Ile Lys Glu Leu Ala Thr Leu Asn Asn Met Ser Glu Pro
                140             145                 150 tat cat ctg agt att gga caa gta ttg aaa att gca aat aat att ccc    1372
Tyr His Leu Ser Ile Gly Gln Val Leu Lys Ile Ala Asn Asn Ile Pro
            155                 160                 165 gat agc aat atg ata cca aca cag aca ata aat gaa tca gag gtg aca    1420
Asp Ser Asn Met Ile Pro Thr Gln Thr Ile Asn Glu Ser Glu Val Thr
        170                 175                 180 caa aat aca gtc aat gag aca tgg aat gct aat aaa cca aca aat gaa    1468
Gln Asn Thr Val Asn Glu Thr Trp Asn Ala Asn Lys Pro Thr Asn Glu
185                 190                 195 caa atg aaa ccc gtt gct aca cca aca cat tca aca atg cca atc aat    1516
Gln Met Lys Pro Val Ala Thr Pro Thr His Ser Thr Met Pro Ile Asn
200                 205                 210                 215 aaa aca cct cca gcc acc tca aat ata gct tgg att tgg cca aca aat    1564
Lys Thr Pro Pro Ala Thr Ser Asn Ile Ala Trp Ile Trp Pro Thr Asn
                220                 225                 230 gga aaa att att caa gga ttt tcc agt gct gat gga ggc aat aaa ggt    1612
Gly Lys Ile Ile Gln Gly Phe Ser Ser Ala Asp Gly Gly Asn Lys Gly
            235                 240                 245 att gat att agc ggt tct cgt gga caa gct gtt aat gca gca gct gct    1660
Ile Asp Ile Ser Gly Ser Arg Gly Gln Ala Val Asn Ala Ala Ala Ala
        250                 255                 260 gga cga gtt gta tat gcc gga gac gct tta cgt gga tat ggt aat tta    1708
Gly Arg Val Val Tyr Ala Gly Asp Ala Leu Arg Gly Tyr Gly Asn Leu
265                 270                 275 att att att aaa cat aat gac agt tat tta agt gct tat gca cat aat    1756
Ile Ile Ile Lys His Asn Asp Ser Tyr Leu Ser Ala Tyr Ala His Asn
280                 285                 290                 295
```

FIG. 11B

```
gaa agt ata ctc gtc aaa gat cag caa gaa gtt aaa gcg ggt caa caa    1804
Glu Ser Ile Leu Val Lys Asp Gln Gln Glu Val Lys Ala Gly Gln Gln
            300                 305                 310 att gct aaa atg gga agt tct gga aca aac aca atc aaa ctc cat ttt    1852
Ile Ala Lys Met Gly Ser Ser Gly Thr Asn Thr Ile Lys Leu His Phe
                315                 320                 325 gaa att cgt tat aaa ggt caa tca gta gat cca atg aga tat tta cca    1900
Glu Ile Arg Tyr Lys Gly Gln Ser Val Asp Pro Met Arg Tyr Leu Pro
            330                 335                 340 aaa aat taatcctaaa aaaatctgca ccttcatcag ttagttgttt agtccaactt     1956
Lys Asn
    345 ttggggtgca gatcatttca gttatcagct ttttattaac tatttttga aaattgcatt  2016 aggcaaacgt tttcgttccg ataaaaattc ctttataatg tggtcgtttt ttatttttt  2076 gatggatctt ttctatgtta cacattttc gtggcacgcc cgcattatcc aatttttcgtt 2136 taaatcagtt attcagtggt ttcagcaaga taatttaccc att                    2179
```

FIG. 11C

CLONING AND EXPRESSION OF *HAEMOPHILUS SOMNUS* TRANSFERRIN-BINDING PROTEINS

CROSS-REFERENCE TO RELATED APPLICATION

This application is a continuation of U.S. patent application Ser. No. 09/405,728, filed Sep. 24, 1999, now U.S. Pat. No. 6,391,316, which is a continuation-in-part of U.S. patent application Ser. No. 09/267,749, filed Mar. 10, 1999, now abandoned, from which applications priority is claimed pursuant to 35 §U.S.C. 120 and which applications are incorporated herein by reference in their entireties.

TECHNICAL FIELD

The present invention relates generally to bacterial antigens and genes encoding the same. More particularly, the present invention pertains to the cloning, expression and characterization of transferrin-binding proteins from *Haemophilus somnus* (*H. somnus*) and the use of the same in vaccine compositions.

BACKGROUND

*Haemophilus somnus* is a Gram-negative bacterium which causes a number of disease syndromes in cattle, collectively referred to as bovine hemophilosis. The bacterium is commonly associated with thromboembolic meningoencephalitis (ITEME), myocarditis, septicemia, arthritis, and pneumonia (Corbeil, L. B. (1990) *Can. J. Vet. Res.* 54:S57–S62; Harris and Janzen (1990) *Can. Vet. J.* 30:816–822; Humphrey and Stephens (1983) *Vet. Bull.* 53:987–1004). These diseases cause significant economic losses to the farm industry annually.

Conventional vaccines against *H. somnus* infection are either based on killed whole cells or on a protein fraction enriched in outer membrane proteins (OMPs). However, whole cell bacterins and surface protein extracts often contain immunosuppressive components which can render animals more susceptible to infection. Recombinant vaccines containing *H. somnus* lipoproteins, LppA, LppB and LppC, have been described. See, e.g., International Publication No. WO 93/21323, published Oct. 28, 1993. However, there remains a need for efficacious subunit vaccines against *H. somnus* infection.

Iron is an essential element for growth of most microbes. Weinberg, E. D. (1978) *Microbiol. Rev.* 42:45–66 . Even though iron is abundant within mammalian tissues, virtually all iron within the mammalian body is held intracellularly as ferritin or as heme compounds, pools which are generally inaccessible to invading microorganisms. Additionally, the small amount of iron present in extracellular spaces is effectively chelated by high-affinity iron-binding host glycoproteins such as transferrin, present in serum and lymph, and lactoferrin, present in secretory fluids and milk. Otto et al. (1992) *Crit. Rev. Microbiol.* 18:217–233.

Hence, bacterial pathogens have developed specific iron-uptake mechanisms. In many bacterial species, these mechanisms involve the synthesis and secretion of small compounds called siderophores which display high affinity for ferric iron (FeIII). Siderophores are capable of removing transferrin-bound iron to form ferrisiderophore complexes which in turn are recognized by specific iron-repressible membrane receptors and internalized into the bacterium where the iron is released. Crosa, J. H. (1989) *Microbiol. Rev.* 53:517–530. Some gram-negative bacteria do not secrete detectable siderophores when grown in an iron-deficient environment but produce outer membrane proteins that bind directly and specifically to transferrin, thereby allowing iron transport into the bacterial cell. Transferrin binding proteins tend to be highly specific for the transferrin of their natural host. The ability of microorganisms to bind and utilize transferrin as a sole iron source, as well as the correlation between virulence and the ability to scavenge iron from the host, has been shown (Archibald and DeVoe (1979) *FEMS Microbiol. Lett.* 6:159–162; Archibald and DeVoe (1980) *Infect. Immun.* 27:322–334; Herrington and Sparling (1985) *Infect. Immun.* 48:248–251; Weinberg, E. D. (1978) *Microbiol. Rev.* 42:45–66).

Two transferrin-binding proteins, termed transferrin-binding protein 1 and 2 (Tbp1 and Tbp2), respectively, have been identified in bacterial outer membranes. For example, Gonzalez et al. (1990) *Mol. Microbiol.* 4:1173–1179, describes 105 and 56 kDa proteins from *Actinobacillus pleuropneumoniae*, designated porcine transferrin binding protein 1 (pTfBP1) and porcine transferrin binding protein 2 (pTfBP2), respectively. U.S. Pat. Nos. 5,417,971, 5,521,072 and 5,801,018 describe the cloning and expression of two transferrin binding proteins from *A. pleuropneumoniae*, as well as the use of the proteins in vaccine compositions. Schryvers, A. B. (1989) *J. Med. Microbiol.* 29:121–130, describes two putative transferrin-binding proteins isolated from *Haemophilus influenzae*. U.S. Pat. No. 5,708,149 and International Publication No. WO 95/13370, published May 18, 1995, describe the recombinant production of *H. influenzae* Tbp1 and Tbp2. U.S. Pat. Nos. 5,141,743 and 5,292, 869 and International Publication No. WO 90/12591 describe the isolation of transferrin-receptor proteins from *Neisseria meningitidis* and the use of the isolated proteins in vaccine compositions. International Publication No. WO 95/33049, published Dec. 7, 1995, and European Publication No. EP 586,266, describe DNA encoding *N. meningitidis* transferrin binding proteins. Finally, Ogunnariwo et al. (1990) *Microbiol. Path.* 9:397–406, describe the isolation of two transferrin-binding proteins from *H. somnus*.

However, to date, the transferrin binding proteins from *H. somnus* have not been recombinantly produced.

DISCLOSURE OF THE INVENTION

The present invention is based on the discovery of genes encoding *H. somnus* transferrin-binding proteins and the characterization thereof. The proteins encoded by the genes have been recombinantly produced and these proteins, immunogenic fragments and analogs thereof, and/or chimeric proteins including the same, can be used, either alone or in combination with other *H. somnus* antigens, in novel subunit vaccines to provide protection from bacterial infection in mammalian subjects.

Accordingly, in one embodiment, the subject invention is directed to an isolated nucleic acid molecule comprising a coding sequence for an immunogenic *H. somnus* transferrin-binding protein selected from the group consisting of (a) an *H. somnus* transferrin-binding protein 1 and (b) an *H. somnus* transferrin-binding protein 2, or a fragment of the nucleic acid molecule comprising at least 15 nucleotides.

In additional embodiments, the invention is directed to recombinant vectors including the nucleic acid molecules, host cells transformed with these vectors, and methods of recombinantly producing *H. somnus* transferrin-binding proteins.

In still further embodiments, the subject invention is directed to vaccine compositions comprising a pharmaceutically acceptable vehicle and an immunogenic *H. somnus* transferrin-binding protein selected from the group consisting of (a) an *H. somnus* transferrin-binding protein 1, (b) an *H. somnus* transferrin-binding protein 2 and (c) an immunogenic fragment of (a) or (b) comprising at least 5 amino acids, as well as methods of preparing the vaccine compositions.

In yet other embodiments, the present invention is directed to methods of treating or preventing *H. somnus* infections in a mammalian subject. The method comprises administering to the subject a therapeutically effective amount of the above vaccine compositions.

In additional embodiments, the invention is directed to methods of detecting *H. somnus* antibodies in a biological sample comprising:

(a) providing a biological sample;

(b) reacting the biological sample with an immunogenic *H. somnus* transferrin binding protein selected from the group consisting of (a) an *H. somnus* transferrin-binding protein 1, (b) an *H. somnus* transferrin-binding protein 2 and (c) an immunogenic fragment of (a) or (b) comprising at least 5 amino acids, under conditions which allow *H. somnus* antibodies, when present in the biological sample, to bind to the *H. somnus* transferrin-binding protein to form an antibody/antigen complex; and (c) detecting the presence or absence of the complex, thereby detecting the presence or absence of *H. somnus* antibodies in the sample.

In yet further embodiments, the invention is directed to an immunodiagnostic test kit for detecting *H. somnus* infection. The test kit comprises an *H. somnus* transferrin-binding protein selected from the group consisting of (a) an *H. somnus* transferrin-binding protein 1, (b) an *H. somnus* transferrin-binding protein 2 and (c) an immunogenic fragment of (a) or (b) comprising at least 5 amino acids, and instructions for conducting the immunodiagnostic test.

These and other embodiments of the present invention will readily occur to those of ordinary skill in the art in view of the disclosure herein.

BRIEF DESCRIPTION OF THE FIGURES

FIGS. 1A–1B show the nucleotide sequences of the *H. somnus* tbp1 and tbp2 genes (SEQ ID NO:1). The tbp1 gene is found at positions 2891–5803 and the tbp2 gene is found at positions 708–2693.

FIG. 2 is a genetic map of the *H. somnus* tbp Region. Restriction sites are shown.

FIG. 3 shows the complete amino acid sequence of *H. somnus* Tbp1 (SEQ ID NO:2).

FIG. 4 shows the complete amino acid sequence of *H. somnus* Tbp2 (SEQ ID NO:3).

FIG. 5 shows Tbp1-specific serological response, measured as antibody titers, to vaccines containing recombinantly produced *H. somnus* transferrin-binding proteins. Bleed 1 was done preimmunization; Bleed 2 was taken at the time of boost; and Bleed 3 was done prior to challenge.

FIG. 6 shows Tbp2-specific serological response, measured as antibody titers, to vaccines containing recombinantly produced *H. somnus* transferrin-binding proteins. Bleed 1 was done preimmunization; Bleed 2 was taken at the time of boost; and Bleed 3 was done prior to challenge.

FIG. 7 shows mortality in groups of animals administered vaccines containing the recombinantly produced *H. somnus* transferrin-binding proteins.

FIG. 8 depicts mean temperature obtained from animals administered vaccines containing recombinantly produced *H. somnus* transferrin-binding proteins and animals given placebos, as described in the examples. Results following *H. somnus* challenge are shown.

FIG. 9 shows depression scores from animals administered vaccines containing recombinantly produced *H. somnus* transferrin-binding proteins and animals given placebos, as described in the examples. Scores from Days 5–8, post *H. somnus* challenge, are shown.

FIG. 10 shows mean sick scores from animals administered vaccines containing recombinantly produced *H. somnus* transferrin-binding proteins and animals given placebos, as described in the examples. Scores from Days 5–8, post *H. somnus* challenge, are shown.

FIGS. 11A–11C depict a chromosomal fragment (SEQ ID NO:4) which includes the *H. somnus* lppB gene, occurring at positions 872–1906 of the figure, and shows the corresponding LppB amino acid sequence (SEQ ID NO:5).

FIG. 12 depicts the Hopp/Woods antigenicity profile of *H. somnus* mature Tbp1.

FIG. 13 depicts the Kyte-Doolittle hydropathy plot (bottom of figure) and Argos transmembrane helices (top of figure) of *H. somnus* mature Tbp1.

FIG. 14 depicts the Hopp/Woods antigenicity profile of *H. somnus* Tbp2.

FIG. 15 depicts the Kyte-Doolittle hydropathy plot of *H. somnus* Tbp2.

DETAILED DESCRIPTION

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Vols. I, II and III, Second Edition (1989); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

A. Definitions

In describing the present invention, the following terms will be employed, and are intended to be defined as indicated below.

It must be noted that, as used in this specification and the appended claims, the singular forms "a", "an" and "the"

include plural referents unless the content clearly dictates otherwise. Thus, for example, reference to "an *H. somnus* transferrin binding protein" includes a mixture of two or more such proteins, and the like.

The terms "transferrin-binding protein", "TF-binding protein" and "Tbp" (used interchangeably herein) or a nucleotide sequence encoding the same, intends a protein or a nucleotide sequence, respectively, which is derived from an *H. somnus* tbp gene. The nucleotide sequence of two representative *H. somnus* tbp genes, termed "tbp1" and "tbp2" herein, and the corresponding amino acid sequence of the Tbp proteins encoded by these gene, are depicted in the Figures. In particular, FIGS. 1A–1B (SEQ ID NO:1) show the nucleotide sequence of full-length tbp1 (occurring at nucleotide positions 2891–5803, inclusive) and tbp2 (occurring at nucleotide positions 708–2693, inclusive) and FIGS. 3 (SEQ ID NO:2) and 4 (SEQ ID NO:3), show the full-length amino acid sequences of Tbp1 and Tbp2, respectively. However, an *H. somnus* transferrin-binding protein as defined herein is not limited to the depicted sequences as several subtypes of *H. somnus* are known and variations in transferrin-binding proteins will occur between strains of *H. somnus*.

Furthermore, the derived protein or nucleotide sequences need not be physically derived from the gene described above, but may be generated in any manner, including for example, chemical synthesis, isolation (e.g., from *H. somnus*) or by recombinant production, based on the information provided herein. Additionally, the term intends proteins having amino acid sequences substantially homologous (as defined below) to contiguous amino acid sequences encoded by the genes, which display immunological and/or transferrin-binding activity.

Thus, the terms intend full-length, as well as immunogenic, truncated and partial sequences, and active analogs and precursor forms of the proteins. Also included in the term are nucleotide fragments of the gene that include at least about 8 contiguous base pairs, more preferably at least about 10–20 contiguous base pairs, and most preferably at least about 25 to 50, or more, contiguous base pairs of the gene. Such fragments are useful as probes and in diagnostic methods, discussed more fully below.

The terms also include those forms possessing, as well as lacking, the signal sequence, as well as the nucleic acid sequences coding therefor. Additionally, the term intends forms of the transferrin-binding proteins which lack the membrane anchor region, and nucleic acid sequences encoding proteins with such deletions. Such deletions may be desirable in systems that do not provide for secretion of the protein. Furthermore, the transferrin-binding domains of the proteins, may or may not be present. Thus, for example, if the transferrin-binding protein will be used to purify transferrin, the transferrin-binding domain will generally be retained. If the protein is to be used in vaccine compositions, immunogenic epitopes which may or may not include the transferrin-binding domain, will be present.

The terms also include proteins in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the proteins may be modified by combination with other biological materials such as lipids (both those occurring naturally with the molecule or other lipids that do not destroy immunological activity) and saccharides, or by side chain modification, such as acetylation of amino groups, phosphorylation of hydroxyl side chains, oxidation of sulfhydryl groups, glycosylation of amino acid residues, as well as other modifications of the encoded primary sequence.

The proteins of the present invention are normally found in association with lipid moieties. It is likely that the fatty acid moiety present is a palmitic acid derivative. The antigens of the present invention, even though carrying epitopes derived from lipoproteins, do not require the presence of the lipid moiety. Furthermore, if the lipid is present, it need not be a lipid commonly associated with the lipoprotein, so long as the appropriate immunologic response is elicited. In any event, suitable fatty acids, such as but not limited to, palmitic acid or palmitic acid analogs, can be conveniently added to the desired amino acid sequence during synthesis, using standard techniques. For example, palmitoyl bound to S-glyceryl-L-Cys ($Pam_3$-Cys) is commercially available (e.g. through Boehringer Mannheim, Dorval, Quebec) and can easily be incorporated into an amino acid sequence during synthesis. See, e.g. Deres et al. (1989) *Nature* 342:561. This is a particularly convenient method for production when relatively short amino acid sequences are used. Similarly, recombinant systems can be used which will process the expressed proteins by adding suitable fatty acids. Representative systems for recombinant production are discussed further below.

The term therefore intends deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity of the protein, are therefore within the definition of the reference polypeptide.

For example, the polypeptide of interest may include up to about 5–10 conservative or non-conservative amino acid substitutions, or even up to about 15–25 conservative or non-conservative amino acid substitutions, so long as the desired function of the molecule remains intact. In this regard, substitutions occurring in the transmembrane binding domain and the signal sequence normally will not affect immunogenicity. One of skill in the art may readily determine other regions of the molecule of interest that can tolerate change by reference to the Hopp/Woods and Kyte-Doolittle plots shown in FIGS. 12–15 herein.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

By "subunit vaccine composition" is meant a composition containing at least one immunogenic polypeptide, but not all antigens, derived from or homologous to an antigen from a pathogen of interest. Such a composition is substantially free of intact pathogen cells or particles, or the lysate of such cells or particles. Thus, a "subunit vaccine composition" is prepared from at least partially purified (preferably substantially purified) immunogenic polypeptides from the pathogen, or recombinant analogs thereof. A subunit vaccine composition can comprise the subunit antigen or antigens of interest substantially free of other antigens or polypeptides from the pathogen.

The term "epitope" refers to the site on an antigen or hapten to which specific B cells and/or T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that resistance of the mammary gland to new infection will be enhanced and/or the clinical severity of the disease reduced. Such protection will be demonstrated by either a reduction or lack of symptoms normally displayed by an infected host and/or a quicker recovery time.

Figure 12:
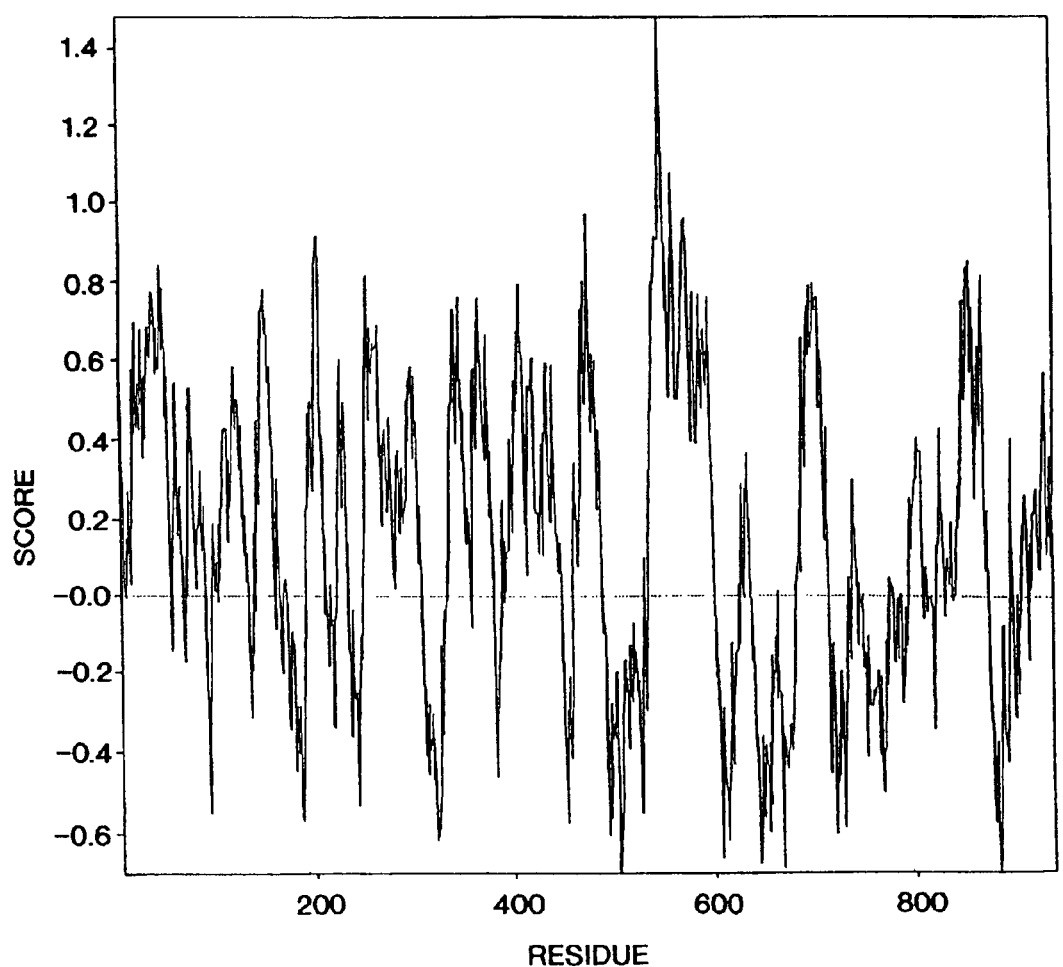
Figure 13:
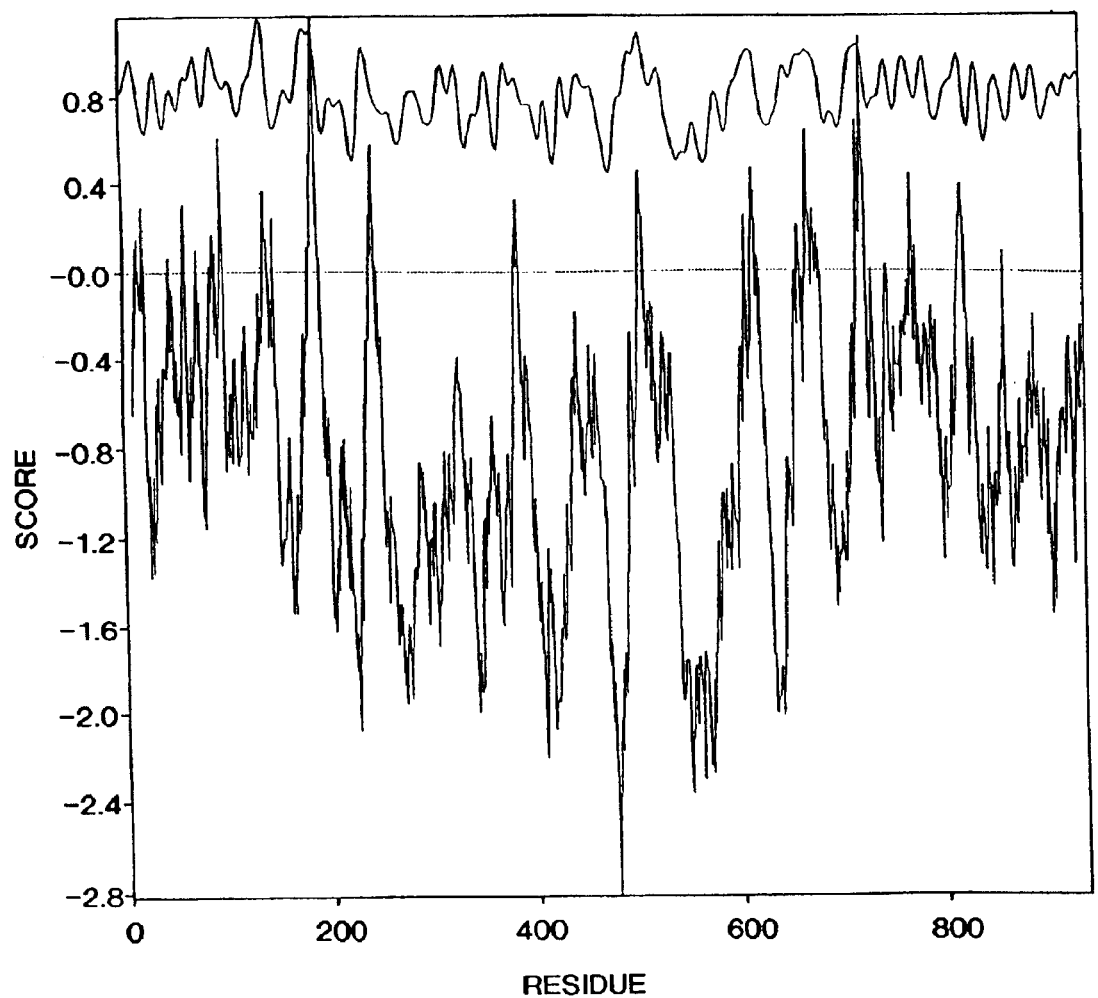
Figure 14:
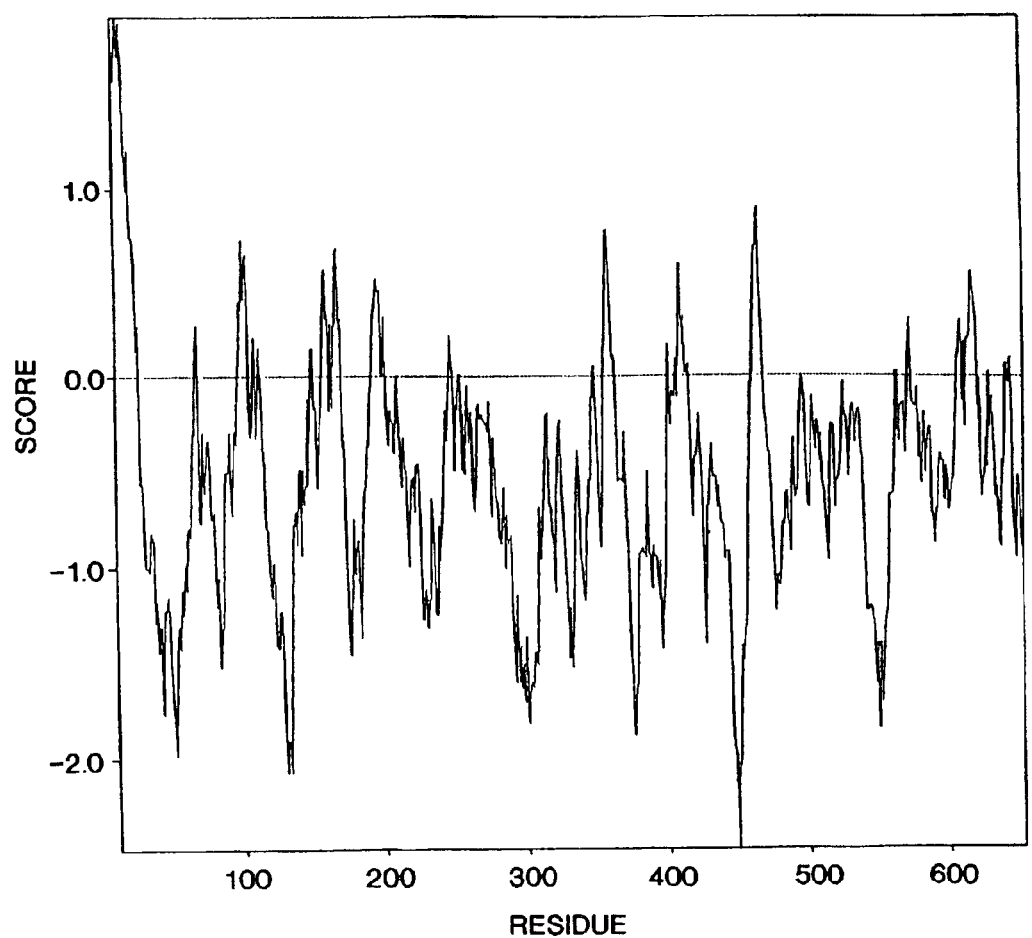
Figure 15:
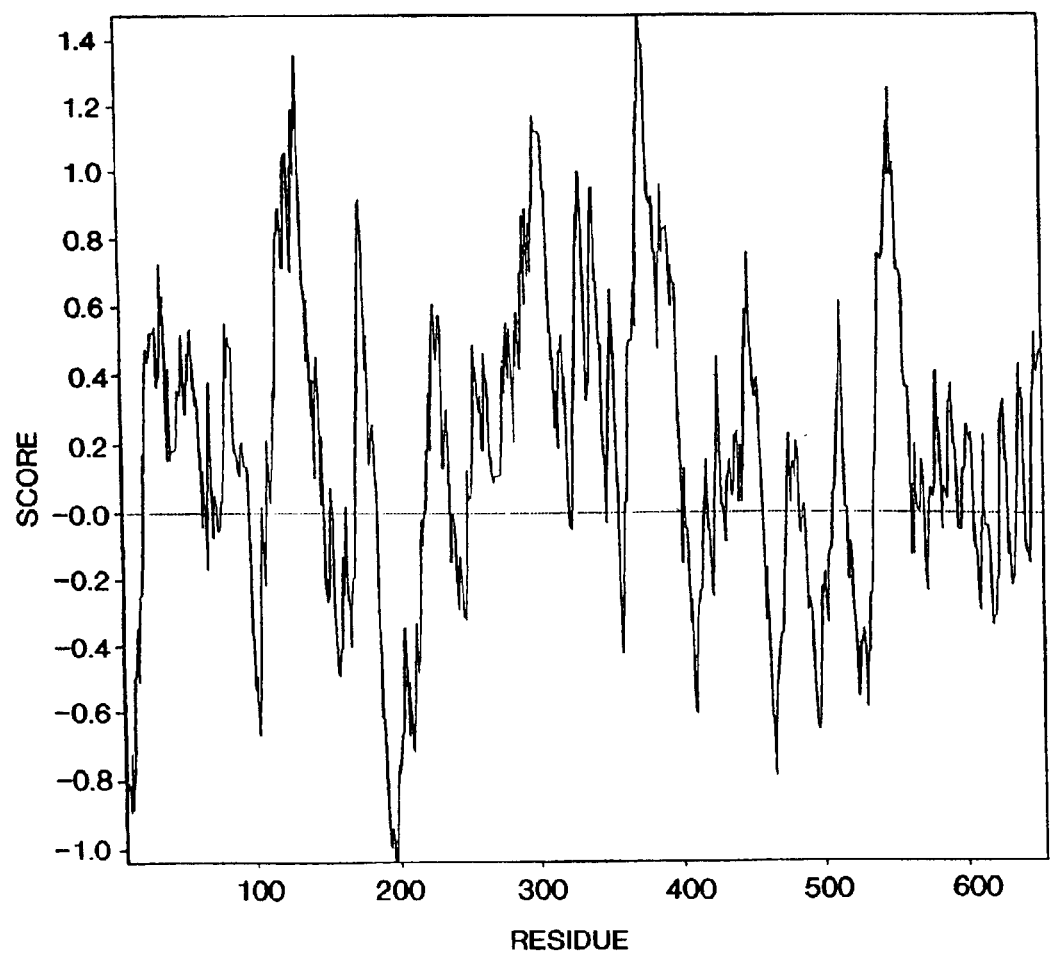

The terms "immunogenic" protein or polypeptide refer to an amino acid sequence which elicits an immunological response as described above. An "immunogenic" protein or polypeptide, as used herein, includes the full-length sequence of the transferrin-binding protein in question, with or without the signal sequence, membrane anchor domain and/or transferrin-binding domain, analogs thereof, or immunogenic fragments thereof. By "immunogenic fragment" is meant a fragment of a transferrin-binding protein which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots. FIGS. 12–14 herein depict Hopp/Woods and Kyte-Doolittle profiles for representative proteins encompassed by the invention.

Immunogenic fragments, for purposes of the present invention, will usually include at least about 3 amino acids, preferably at least about 5 amino acids, more preferably at least about 10–15 amino acids, and most preferably 25 or more amino acids, of the parent transferrin-binding protein molecule. There is no critical upper limit to the length of the fragment, which may comprise nearly the full-length of the protein sequence, or even a fusion protein comprising two or more epitopes of Tbp1 and/or Tbp2.

"Native" proteins or polypeptides refer to proteins or polypeptides isolated from the source in which the proteins naturally occur. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "vector" is a replicon, such as a plasmid, phage, or cosmid, to which another DNA segment may be attached so as to bring about the replication of the attached segment.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Homology" refers to the percent identity between two polynucleotide or two polypeptide moieties. Two DNA, or two polypeptide sequences are "substantially homologous" to each other when the sequences exhibit at least about 80%–85%, preferably at least about 90%, and most preferably at least about 95%–98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman (1981) *Advances in Appl. Math.* 2:482–489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter= none; strand=both; cutoff=60; expect=10; Matrix= BLOSUM62; Descriptions=50 sequences; sort by=HIGH SCORE; Databases=non-redundant, GenBank+EMBL+ DDBJ+PDB+GenBank CDS translations+Swiss protein+ Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

The term "functionally equivalent" intends that the amino acid sequence of a transferrin-binding protein is one that will elicit a substantially equivalent or enhanced immunological response, as defined above, as compared to the response elicited by a transferrin-binding protein having identity with the reference transferrin-binding protein, or an immunogenic portion thereof.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

The term "treatment" as used herein refers to either (i) the prevention of infection or reinfection (prophylaxis), or (ii) the reduction or elimination of symptoms of the disease of interest (therapy).

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and $\alpha$-$\beta$-galactosidase.

B. General Methods

Central to the present invention is the discovery of genes encoding two *H. somnus* transferrin-binding proteins, termed "Tbp1" and "Tbp2," respectively herein. In particular, the genes for *H. somnus* transferrin-binding protein 1 ("tbp1") and *H. somnus* transferrin-binding protein 2 ("tbp2") have been isolated, sequenced and characterized, and the protein sequences for Tbp1 and Tbp2 deduced therefrom. The complete DNA sequences are shown in FIGS. 1A–1B and the protein sequences for Tbp1 and Tbp2 shown in FIGS. 3 (SEQ ID NO:2) and 4 (SEQ ID NO:3), respectively.

As described in the examples, full-length tbp1, depicted at nucleotide positions 2891–5803, inclusive, of FIGS. 1A–1B, encodes a full-length Tbp1 protein of approximately 971 amino acids, shown as amino acids 1–971, inclusive, of FIG. 3 (SEQ ID NO:2). The protein has a predicted molecular weight of about 109,725 kDa. The full-length sequence includes a signal peptide of 28 amino acids, occurring at positions 1 to 28 of FIG. 3. Thus, the mature Tbp1 sequence is represented by amino acids 29 to 971, inclusive, of FIG. 3 and is encoded by the nucleotide sequence depicted at positions 2975 to 5803, inclusive of FIGS. 1A–1B. FIG. 12 shows the Hopp/Woods antigenicity profile of *H. somnus* mature Tbp1. FIG. 13 depicts the Kyte-Doolittle hydropathy plot (bottom of figure) and Argos transmembrane helices (top of figure) of *H. somnus* mature Tbp1.

Full-length tbp2, depicted at nucleotide positions 708–2693, inclusive, of FIGS. 1A–1C (SEQ ID NO:1), encodes a full-length Tbp2 protein of approximately 662 amino acids, shown as amino acids 1–662, inclusive, of FIG. 4 (SEQ ID NO:3). The protein has a predicted molecular weight of about 71,311 kDa. The full-length sequence includes a signal peptide of 19 amino acids, occurring at positions 1 to 19 of FIG. 4. Thus, the mature Tbp2 sequence is represented by amino acids 20 to 662, inclusive, of FIG. 4 and is encoded by the nucleotide sequence depicted at positions 765 to 2683, of FIGS. 1A–1B. FIG. 14 depicts the Hopp/Woods antigenicity profile of *H. somnus* Tbp2 and FIG. 15 depicts the Kyte-Doolittle hydropathy plot of *H. somnus* Tbp2. Unlike Tbp1, no transmembrane binding domains are present in the Tbp2 molecule.

The *H. somnus* transferrin-binding proteins, immunogenic fragments thereof or chimeric proteins including one or more epitopes of Tbp1 and Tbp2, can be provided, either alone or in combination, in subunit vaccine compositions to treat or prevent bacterial infections caused by *H. somnus*, including, but not limited to, hemophilosis, thromboembolic meningoencephalitis (ITEME), septicemia, arthritis, and pneumonia (Corbeill, L. B., *Can. J. Vet. Res.* (1990) 54:S57–S62; Harris, F. W., and Janzen, E. D., *Can. Vet. J.* (1990) 30:816–822; Humphrey, J. D., and Stephens, L. R., *Vet. Bull.* (1983) 53:987–1004), as well as myocarditis, pericarditis, spontaneous abortion, infertility and mastitis.

In addition to use in vaccine compositions, the proteins and fragments thereof, antibodies thereto, and genes coding therefor, can be used as diagnostic reagents to detect the presence of infection in a mammalian subject. Similarly, the genes encoding the proteins can be cloned and used to design probes to detect and isolate homologous genes in other bacterial strains. For example, fragments comprising at least about 15–20 nucleotides, more preferably at least about 20–50 nucleotides, and most preferably about 60–100 or more nucleotides, will find use in these embodiments. The *H. somnus* transferrin-binding proteins also find use in purifying transferring from *Haemophilus* species and from recombinant host cells expressing the same.

*H. somnus* transferrin binding proteins can be used in vaccine compositions either alone or in combination with other bacterial, fungal, viral or protozoal antigens. These antigens can be provided separately or even as fusion proteins comprising one or more epitopes of the transferrin-binding proteins fused together and/or to one or more of the above antigens.

For example, other immunogenic proteins from *H. somnus* can be used in the subject vaccines, including, but not limited to, *H. somnus* LppA, LppB and/or LppC polypeptides, *H. somnus* haemin-binding protein, and *H. somnus* haemolysin. All of these *H. somnus* proteins are described in International Publication No. WO 93/21323, published Oct. 28, 1993). For example, FIGS. 11A–11C depict the *H. somnus* LppB protein (SEQ ID NO:5) and the gene coding therefor (positions 872–1906 of SEQ ID NO:4). The *H. somnus* LppB preprotein is encoded by nucleotide positions 872 through 1906 (amino acid residues 1 through 345) and the mature protein is encoded by nucleotide positions 920 through 1906 (amino acid residues 17 through 345). The entire LppB protein, or fragments comprising immunogenic polypeptides of the protein, can be used in vaccine compositions in combination with either or both of the *H. somnus* transferrin binding proteins.

Production of Transferrin-binding Proteins

The above described transferrin-binding proteins and active fragments, analogs and chimeric proteins derived from the same, can be produced by a variety of methods. Specifically, transferrin-binding proteins can be isolated directly from bacteria which express the same. The proteins can be isolated directly from *H. somnus* from outer membrane preparations, using standard purification techniques. See, e.g. Theisen and Potter (1992) *Infect. Immun.* 60:826–831. The desired proteins can then be further purified i.e. by column chromatography, HPLC, immunoadsorbent techniques or other conventional methods well known in the art.

Alternatively, the proteins can be recombinantly produced as described herein. As explained above, these recombinant products can take the form of partial protein sequences, full-length sequences, precursor forms that include signal sequences, mature forms without signals, or even fusion proteins (e.g., with an appropriate leader for the recombinant host, or with another subunit antigen sequence for *H. somnus* or another pathogen).

The tbp genes of the present invention can be isolated based on the ability of the protein products to bind transferrin, using transferrin-binding assays as described below. Thus, gene libraries can be constructed and the resulting clones used to transform an appropriate host cell. Colonies can be pooled and screened for clones having transferrin-binding activity. Colonies can also be screened using polyclonal serum or monoclonal antibodies to the transferrin-binding protein.

Alternatively, once the amino acid sequences are determined, oligonucleotide probes which contain the codons for a portion of the determined amino acid sequences can be prepared and used to screen genomic or cDNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; Sambrook et al., supra. Once a clone from the screened library has been identified by positive hybridization, it can be confirmed by restriction enzyme analysis and DNA sequencing that the particular library insert contains a transferrin-binding protein gene or a homolog thereof. The genes can then be further isolated using standard techniques and, if desired, PCR approaches or restriction enzymes employed to delete portions of the full-length sequence.

Similarly, genes can be isolated directly from bacteria using known techniques, such as phenol extraction and the sequence further manipulated to produce any desired alterations. See, e.g., Sambrook et al., supra, for a description of techniques used to obtain and isolate DNA.

Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, Sambrook et al., supra; *DNA Cloning*, supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If a signal sequence is included, it can either be the native, homologous sequence, or a heterologous sequence. For example, the signal sequence for the particular *H. somnus* transferrin-binding protein, can be used for secretion thereof, as can a number of other signal sequences, well known in the art. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the transferrin-binding protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis. Chemical synthesis of peptides may be preferable if a small fragment of the antigen in question is capable of raising an immunological response in the subject of interest.

The transferrin-binding proteins of the present invention, or their fragments, can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) *J. Chrom.* 348:363–370. If serum containing polyclonal antibodies is used, the polyclonal antibodies can be purified by immunoaffinity chromatography, using known procedures.

Monoclonal antibodies to the transferrin-binding proteins and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the transferrin-binding proteins, or fragments thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response. Polyclonal and monoclonal antibodies are also useful for diagnostic purposes.

Vaccine Formulations and Administration

The transferrin-binding proteins of the present invention can be formulated into vaccine compositions, either alone, in combination and/or with other antigens, for use in immunizing subjects as described below. Methods of preparing such formulations are described in, e.g., *Remington's Pharmaceutical Sciences*, Mack Publishing Company, Easton, Pa., 18 Edition, 1990. Typically, the vaccines of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Adjuvants may include for example, muramyl dipeptides, avridine, aluminum hydroxide, dimethyldioctadecyl ammonium bromide (DDA), oils, oil-in-water emulsions, saponins, cytokines, and other substances known in the art.

The transferrin-binding proteins may be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The transferrin-binding proteins may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the transferrin-binding proteins of the present invention include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

Furthermore, the transferrin-binding proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Vaccine formulations will contain a "therapeutically effective amount" of the active ingredient, that is, an amount capable of eliciting an immune response in a subject to which the composition is administered. In the treatment and prevention of *H. somnus* infection, for example, a "therapeutically effective amount" would preferably be an amount that enhances resistance of the mammal in question to new infection and/or reduces the clinical severity of the disease. Such protection will be demonstrated by either a reduction or lack of symptoms normally displayed by an infected host and/or a quicker recovery time.

The exact amount is readily determined by one skilled in the art using standard tests. The transferrin-binding protein concentration will typically range from about 1% to about 95% (w/w) of the composition, or even higher or lower if appropriate. With the present vaccine formulations, 5 to 500 $\mu$g of active ingredient per ml of injected solution, preferably 10 to 100 $\mu$g of active ingredient per ml, should be adequate to raise an immunological response when a dose of 1 to 3 ml per animal is administered.

To immunize a subject, the vaccine is generally administered parenterally, usually by intramuscular injection. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered as many doses as is required to maintain a state of immunity to infection.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The transferrin-binding proteins can also be delivered using implanted mini-pumps, well known in the art.

The transferrin-binding proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK-recombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the subject transferrin-binding proteins can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see U.S. Pat. Nos. 5,580,859 and 5,589,466; International Publication No. WO/90/11092; and Wolff et al. (1990) *Science* 247:1465–1468). Liposome-mediated gene transfer can also be accomplished using known methods. See, e.g., U.S. Pat. No. 5,703,055; Hazinski et al. (1991) *Am. J. Respir. Cell Mol. Biol.* 4:206–209; Brigham et al. (1989) *Am. J. Med. Sci.* 298:278–281; Canonico et al. (1991) *Clin. Res.* 39:219A; and Nabel et al. (1990) *Science* 249:1285–1288. Targeting agents, such as antibodies directed against surface antigens expressed on specific cell types, can be covalently conjugated to the liposomal surface so that the nucleic acid can be delivered to specific tissues and cells susceptible to infection.

Diagnostic Assays

As explained above, the transferrin-binding proteins of the present invention may also be used as diagnostics to detect the presence of reactive antibodies of *H. somnus* in a biological sample in order to determine the presence of *H. somnus* infection. For example, the presence of antibodies reactive with transferrin-binding proteins can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more transferrin-binding proteins) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2–13; Hashida et al., *J. Appl. Biochem.* (1984) 6:56–63; and Anjaneyulu and Staros, *International J. of Peptide and Protein Res.* (1987) 30:117–124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with a transferrin-binding protein. A biological sample containing or suspected of containing anti-transferrin-binding protein immunoglobulin molecules is then added to the coated wells. After a period of incubation sufficient to allow antibody binding to the immobilized antigen, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-transferrin-binding antigen ligands from a biological sample can be readily detected using a secondary binder comprising an antibody directed against the antibody ligands. A number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the transferrin-binding proteins and antibodies specific for those proteins form complexes under precipitating conditions. In one particular embodiment, transferrin-binding proteins can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for the transferrin-binding proteins. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing anti-transferrin-binding molecules is immobilized to a substrate. In this regard, an initial affinity purification of the sample can be carried out using immobilized antigens. The resultant sample preparation will thus only contain anti-$H.$ $somnus$ moieties, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled transferrin-binding proteins are contacted with the bound antibodies under suitable binding conditions. After any non-specifically bound antigen has been washed from the immunoaffinity support, the presence of bound antigen can be determined by assaying for label using methods known in the art.

Additionally, antibodies raised to the transferrin-binding proteins, rather than the transferrin-binding proteins themselves, can be used in the above-described assays in order to detect the presence of antibodies to the proteins in a given sample. These assays are performed essentially as described above and are well known to those of skill in the art.

The above-described assay reagents, including the transferrin-binding proteins, or antibodies thereto, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Below are examples of specific embodiments for carrying out the present invention. The examples are offered for illustrative purposes only, and are not intended to limit the scope of the present invention in any way.

C. Experimental

EXAMPLE 1

Isolation and Cloning of $H.$ $somnus$ tbp1 and tbp2

Materials and Methods

Bacterial Strains, Plasmids and Growth Conditions.

$E.$ $coli$ DH5αF'IQ[φ80 lacZΔM15 endA1 recA1 hsdR17 ($r_K^-$ $m_K^+$) supE44 thi-1 λ$^-$ gyrA96 rel A1 Δ(lacZYA-argF) U169/F' lacI$^q$ proAB$^+$ lacZΔM15 zzf::Tn5 (Km$^r$ )] (available commercially from, e.g., Stratagene), and JM105 (Sambrook, Fritsch & Maniatis, *Molecular Cloning: A Laboratory Manual*, Vols. I, II and III, Second Edition (1989)) were from the laboratory collection. $E.$ $coli$ strains were grown aerobically at 37° C. in Luria-Bertani (LB) or in M63 defined medium containing 0.5% (vol/vol) glycerol supplemented with 2% (wt/vol) casamino acids. Ampicillin was used at 50 μg/ml. $H.$ $somnus$ strain HS25 was obtained from the lung of a calf which died of pneumonia and has been shown to induce experimental hemophilosis in calves. The conditions for the storage and growth of $H.$ $somnus$ have been described previously. Theisen and Potter (1992) *J. Bacteriol.* 174:17–23. Liquid cultures were made in brain heart infusion broth (Difco laboratories, Detroit, Mich.) supplemented with 0.1% (wt/vol) Tris base and 0.001% (wt/vol) thiamine monophosphate (BHI-TT). Growth in iron-deplete conditions was obtained by adding the iron chelator 2,2'-dipyridyl at a final concentration of 300 μM to the BHI-TT medium.

The expression library consisted of 2- to 7-kb partial Sau3A1 restriction fragments of $H.$ $somnus$ genomic DNA ligated into the BamHI restriction site of pGH432 (see, Theisen and Potter (1992) *J. Bacteriol.* 174:1714 23), allowing for in-frame fusions with an artificial leader peptide whose expression can be induced from a lacO controlled tac promoter (Advanced Vectors, Hopkins, Minn.).

Preparation of the Native Transferrin Receptors of $H.$ $somnus$ and Specific Antisera.

Transferrin-binding proteins (Tbp) from $H.$ $somnus$ strain HS25 were isolated by affinity chromatography using bovine transferrin as described by ogunnariwo et al. (1990) *Microbiol. Path.* 9:397–406. Briefly, total membranes of $H.$ $somnus$ were mixed with biotinylated bovine transferrin before solubilization with EDTA-Sarkosyl and addition to streptavidin-agarose. The affinity bound material was released by washing with various buffers. Specific antiserum against the transferrin-binding proteins was raised in a rabbit by conventional methods.

PAGE and Immunoblotting.

SDS-polyacrylamide gel electrophoresis (PAGE) of proteins was performed using the method described by Laemmli (Laemmli, U.K. (1970) Nature 227:680–685). Immunoblotting was carried out using standard techniques described by the manufacturer of the electroblot apparatus (BioRad Laboratories). The primary antiserum was rabbit serum raised against H. somnus Tbp purified by affinity chromatography or bovine hyperimmune serum raised against live H. somnus HS25 (Theisen and Potter (1992) J. Bacteriol. 174:17–23). The seroreactive proteins were detected with goat anti-rabbit immunoglobulin G coupled to alkaline phosphatase (PhoA) or with goat anti-bovine immunoglobulin G coupled to PhoA (Kirkegaard & Perry Laboratories, Inc., Gaithersburg, Md.). PhoA activity was visualized using the nitroblue tetrazolium-BCIP system (Promega, Madison, Wis.).

Colony Immunoblot of an H. somnus Genomic Library.

JM105 cells harboring the plasmid expression library of H. somnus HS25 were streaked on agar plates and tested for the production of Tbp by the colony blot method (French et al. (1986) Anal. Biochem. 156:417–423) using rabbit serum raised against affnity-purified H. somnus Tbp.

DNA Techniques.

Standard methods were used for DNA manipulations (Sambrook, supra). The DNA restriction enzyme digests were done in T4 DNA polymerase buffer (Sambrook, supra) with 1 mM dithiothreitol and supplemented with 3 mM spermidine. All synthetic oligonucleotides were produced with a Gene Assembler Plus (Pharmacia LKB Biotechnology, Uppsala, Sweden) DNA synthesizer. DNA sequencing was performed by the dideoxy chain-termination method (Sanger et al. (1977) Proc. Natl. Acad. Sci. USA 74:5463–5467; T7 sequencing kit (Pharmacia)) on single stranded DNA derived from nested deletions prepared by exonuclease III treatment (Henikoff, S. (1977) Gene 28:351–359; double-stranded nested deletion kit (Pharmacia)) or double stranded DNA as template. Sequences were analysed with the PCGENE software package (IntelliGenetics, Mountain View, Calif.).

Inverse PCR, based on the method of Ochman et al. (Ochman et al. (1990) "Amplification of flanking sequences by inverse PCR." in PCR Protocols: A Guide to Methods and Applications. Academic Press) was used for cloning tbp2 from H.somnus HS25.

Enrichment of Recombinantly Produced Tbp1 and Tbp2 from E. coli

For Tbp1, Bacteria were grown to mid-log phase in one liter of L-broth supplemented with 50 $\mu$g/ml of ampicillin. When the absorbance at 600 nm reached 0.6, isopropyl-$\beta$, D-thiogalactoside (IPTG) was added to a final concentration of 1 mM and the cultures were incubated with vigorous agitation for 2 h at 37° C. The bacteria were harvested by centrifugation, resuspended in 40 ml of 25% sucrose/50 mM Tris-HCl buffer (pH 8) and frozen at −70° C. The frozen cells were thawed at room temperature and 10 ml of lysozyme (10 mg/ml in 250 mM Tris-HCl, pH 8) was added. After 15 minutes on ice, 300 ml of detergent mix (5 parts of 20 mM Tris-HCl, pH 7.4/300 mM sodium chloride/2% deoxycholic acid/2% Nonidet-P40 and 4 parts of 100 mM Tris-HCl, pH 8/50 mM EDTA/2% Triton X-100) were added. The viscosity was reduced by sonication and protein aggregates were harvested by centrifugation at 27,000× g for 15 minutes. The pellets were dissolved in a minimal volume of 4 M guanidine hydrochloride. The proteins were analyzed by sodium dodecyl sulfate-polyacrylamide gel electrophoresis and the protein concentration was estimated by comparing the intensity of the Coomassie blue-stained bands to a bovine serum albumin standard.

Tbp2 was purified from total outer membranes with Sarkosyl. Briefly, bacteria were grown to mid-log phase in one liter of L-broth supplemented with ampicillin. When the absorbance at 600 nm reached approximately 0.6, IPTG was added to a final concentration of 1 mM and the cultures were incubated with vigorous agitation for 2–4 h at 37° C. The bacteria were harvested by centrifugation, resuspended in Tris-EDTA buffer, pH 8, and treated with lysozyme as described above. Cells were disrupted by sonication and insoluble cell debris was removed by centrifugation. The supernatant was then layered on a sucrose gradient and the outer membrane protein band withdrawn with a syringe following overnight centrifugation. Following dialysis, lipoproteins including Tbp2, were selectively solubilized by mixing the membrane fragments with sarkosyl. In the presence of this detergent, lipid-modified proteins remain soluble while the outer membrane fragments are precipitated and can be removed by ultracentrifugation.

Labelling of Proteins with [$^3$H]Palmitate and Globomycin Treatment.

Exponentially growing cells (4×10$^8$ cells per ml) of H. somnus strain HS25 in BHI-TT and of E. coli DH5$\alpha$F' IQ harboring the specified plasmids in M63 defined medium were incubated for 2 h at 37° C. with [$^3$H]palmitate at a final concentration of 50 $\mu$Ci/ml, in the absence or presence of globomycin (100 $\mu$g/ml), a specific inhibitor of prolipoprotein signal peptidase II (Dev et al. (1985) J. Biol. Chem. 260:5891–5894) as described previously (Theisen et al. (1992) Infect. Immun. 62:826–831). Labelling was terminated by precipitation with trichloroacetic acid (10%, wt/vol) for 30 min on ice. Proteins were pelleted by centrifugation at 15,000× g for 20 min and washed twice with methanol to remove lipids. The proteins, resuspended in sample buffer, were analyzed by SDS-PAGE and the radiolabelled protein bands in the dried gel were detected by fluorography.

Fractionation of H. somnus Cells and Preparation of Outer Membranes.

Exponentionally growing H. somnus HS25 cells were lysed by two passages through a French pressure cell. Separation of the various cellular fractions, including Sarkosyl-insoluble outer membranes (Filip et al. (1973) J. Bacteriol. 115:717–722) was done by differential centrifugation as previously described (Rioux et al. (1992) Gene 116:13–20). The proteins from cell lysates and various fractions were precipitated at 10% (wt/vol) trichloroacetic acid for 40 min on ice, pelleted by centrifugation at 15,000× g for 20 min, and washed twice with methanol to remove lipids before analysis by SDS-PAGE.

Results

In order to identify clones expressing Tbp epitopes, a genomic expression library of H. somnus strain HS25 in E. coli was screened with polyclonal antiserum raised against affinity-purified Tbp1 and Tbp2 of H. somnus. This anti-Tbp antiserum reacted with proteins with relative molecular weights of 80,000 and 115,000, respectively (termed Tbp2 and Tbp1, respectively, herein).

A clone carrying a 4.1-kilobase pair DNA insert was obtained. The analysis of the nucleotide sequence of the DNA insert showed the presence of a truncated open reading frame coding for a predicted polypeptide similar to the carboxyl region of predicted Tbp1 polypeptides of Neisseria meningitidis and Neisseria gonorrhoeae. A polypeptide with $M_r$ of approximately 110,000 was produced by the clone;

this polypeptide was recognized by bovine hyperimmune serum against live *H. somnus* HS25.

The DNA region coding for the amino terminus of *H. somnus* Tbp1 was obtained by using the method of inverse polymerase chain reaction. The complete tbp1 ORF codes for a 971 amino acid polypeptide with predicted molecular weight of 109,725. The reading frame and a putative cleavage site of signal peptidase I were confirmed by the partial amino acid sequence obtained from N-terminal microsequencing of the mature form of native *H. somnus* Tbp1. The molecule includes a signal peptide of 28 amino acids.

The tbp1 gene region coding for the mature Tbp1 was subcloned into an *E. coli* expression vector pGH432, containing a tac promoter to give plasmid pCRR41 (ATCC Accession No. 98810) which expressed the *H. somnus* Tbp1 protein as insoluble inclusion bodies following induction with IPTG, and Tbp1 was partially purified by aggregate preparation.

The gene coding for Tbp2 was isolated by inverse PCR and the sequence coding for the entire Tbp2 peptide, including the signal sequence, was expressed in the same vector as described above. This plasmid was named pCRR90 (ATCC Accession No. 98811). Following IPTG induction, the Tbp2 protein was extracted from total *E. coli* outer membranes with Sarkosyl, as described above. Unlike other membrane proteins, Tbp2 remained soluble in this detergent due to its lipid modification.

The genes coding for Tbp1 and Tbp2, plus flanking DNA are shown in FIGS. 1A–1B. Two open reading frames were found, one starting at nucleotide 708 and ending at position 2693 (Tbp2) and the second starting at nucleotide 2891 and ending at position 5803 (Tbp1) (see FIG. 2). The predicted amino acid sequences of these two proteins are shown in FIG. 3 (Tbp1) and FIG. 4 (Tbp2). The full-length Tbp1 sequence includes a signal peptide of 28 amino acids, occurring at positions 1 to 28 of FIG. 3. Thus, the mature Tbp1 sequence is represented by amino acids 29 to 971, inclusive, of FIG. 3 and is encoded by the nucleotide sequence depicted at positions 2975 to 5803, inclusive of FIGS. 1A–1B.

The full-length Tbp2 sequence includes a signal peptide of 19 amino acids, occurring at positions 1 to 19 of FIG. 4. Thus, the mature Tbp2 sequence is represented by amino acids 20 to 662, inclusive, of FIG. 4 and is encoded by the nucleotide sequence depicted at positions 765 to 2683, of FIGS. 1A–1B.

EXAMPLE 2

Protective Efficacy of Recombinant

Transferrin-Binding Proteins

The Tbp1 and Tbp2 proteins were produced recombinantly in *E. coli* as inclusion bodies and as a membrane bound protein, respectively. As explained above, Tbp1 inclusion bodies were prepared using standard procedures while soluble Tbp2 was prepared from *E. coli* outer membranes. These membranes were then subjected to a sarkosyl extraction in order to preferentially solubilize Tbp2.

Vaccines were formulated using the adjuvant VSA3 (a combination of DDA (Kodak) and Emulsigen-Plus (MVP Laboratories, Omaha, Nebr.)) such that the volume of each dose was 2 cc containing 50 $\mu$g of each antigen. A placebo vaccine was also prepared containing sterile diluent in place of antigen. Three groups were included in the trial, one of which received placebo, a second which received two immunizations with Tbp2 and a third which received two immunizations with Tbp1+Tbp2. Each group had eight animals and the interval between primary and secondary immunization was three weeks. All vaccinations were carried out at a farm in southern Saskatchewan and vaccines were delivered via the subcutaneous route.

Two weeks after the second immunization, animals were challenged with bovine herpesvirus-1 followed four days later by aerosol exposure to *H. somnus* strain HS25. Animals were examined daily by a veterinarian and animal health technician and the following data was recorded: weight, temperature, nasal scores, depression, strength, respiratory distress and sickness. Each of these criteria, with the exception of weight and temperature, was scored on a scale of 0–4.

The serological response to vaccination was measured using an enzyme-linked immunosorbent assay (ELISA). Serum samples were collected at the time of the first and second immunizations plus on the day of challenge with BHV-1. The titers are presented as the reciprocal of the serum dilution which resulted in an optical density equivalent to the background plus two standard deviations.

None of the animals showed any adverse response to immunization with any of the formulations used. The serological response to vaccination was determined using an ELISA procedure which measured the serum antibody levels to Tbp1 and Tbp2. An *H. somnus* outer membrane extract was also used as an antigen but no significant increase in titer was observed. This is not unexpected, since the level of iron-regulated outer membrane proteins in this antigen preparation is extremely low.

Figure 5:
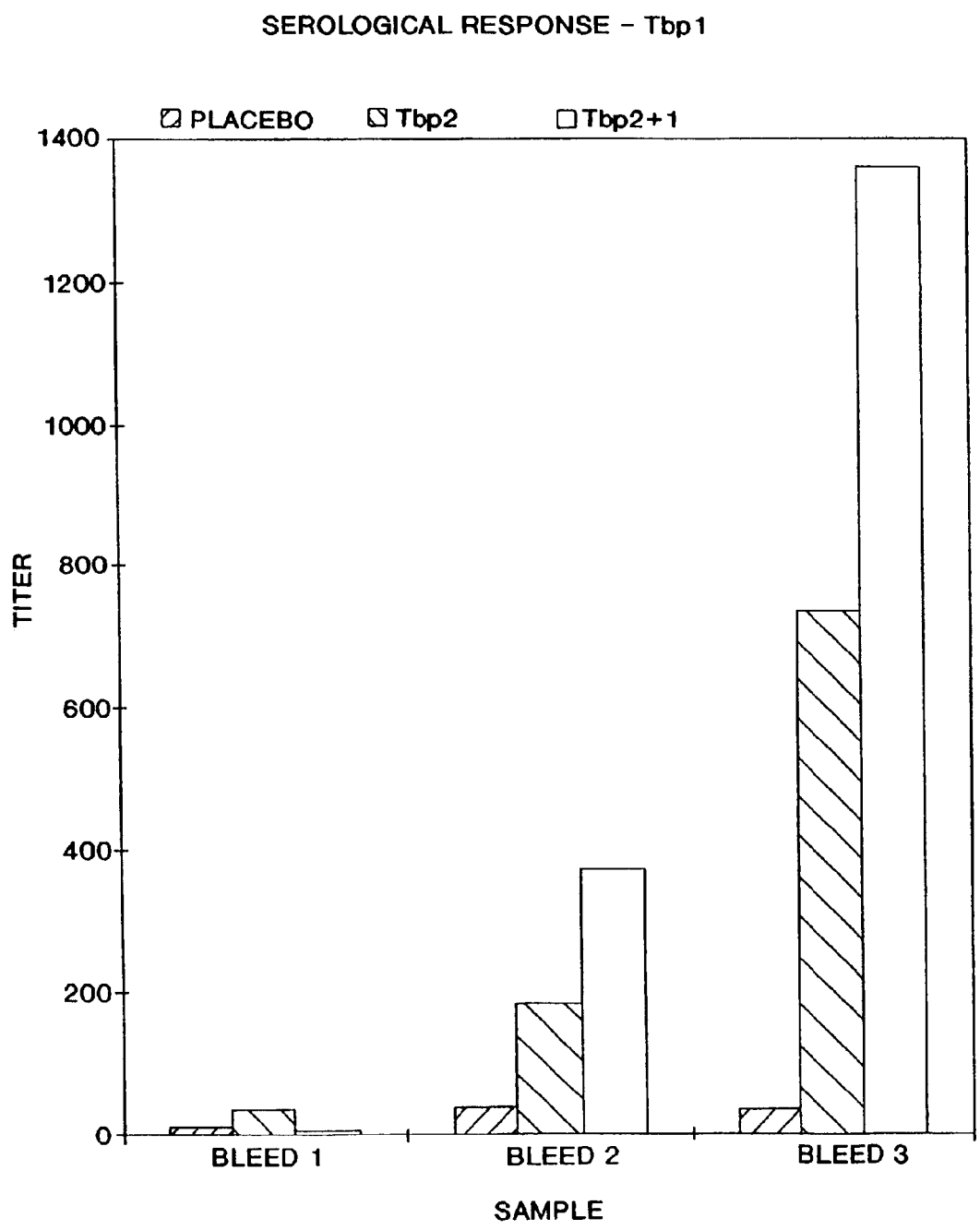
Figure 6:
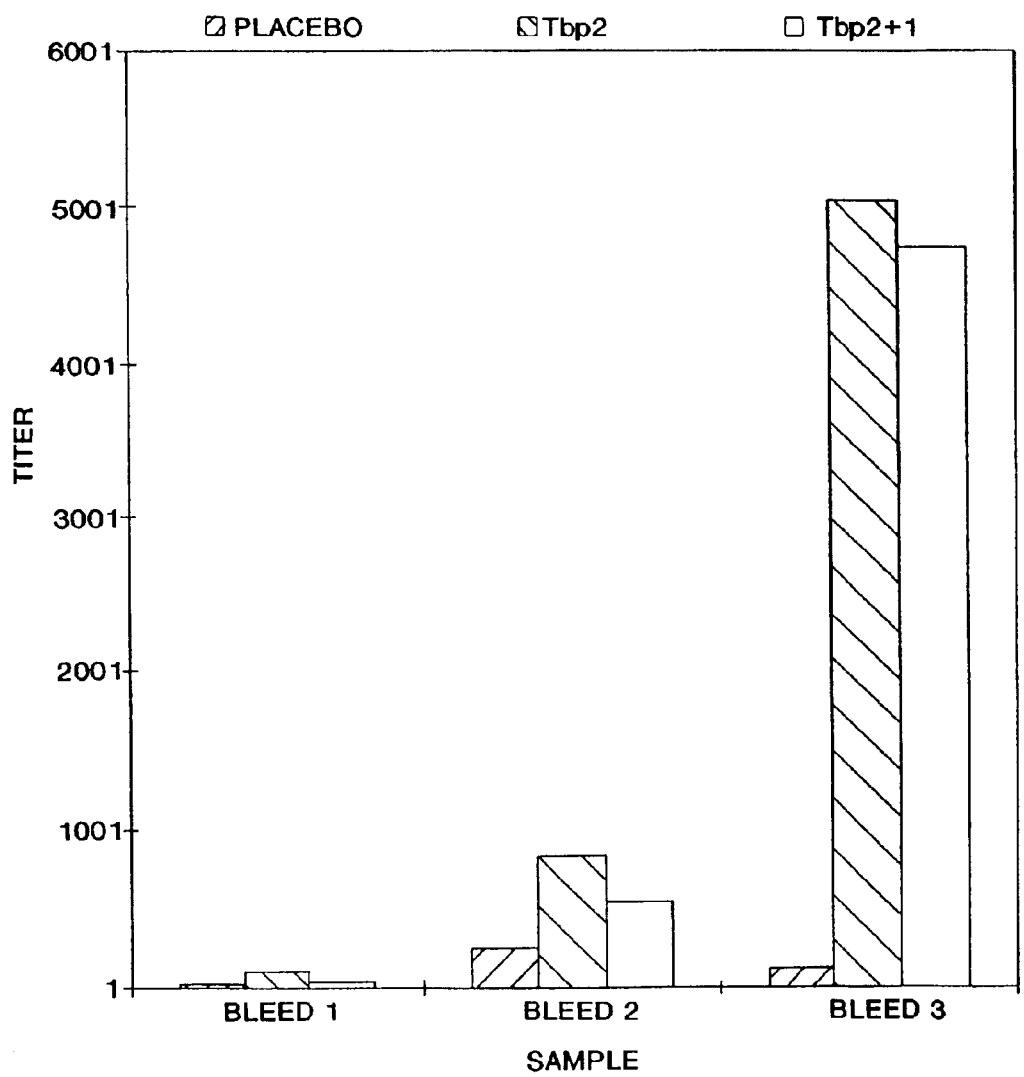

The antibody titers against Tbp1 and Tbp2 are shown in FIGS. 5 and 6, respectively. It can be seen that animals receiving recombinant Tbp2 vaccines responded well to this antigen, with no significant difference between Groups 2 and 3. The response against Tbp1 was minimal, as expected based on our experience with this antigen from our other organisms. The group which received only Tbp2 also had serum antibody levels against Tbp1, but this was probably due to contaminating *E. coli* proteins present in the antigen preparation used for the ELISA.

Figure 7:
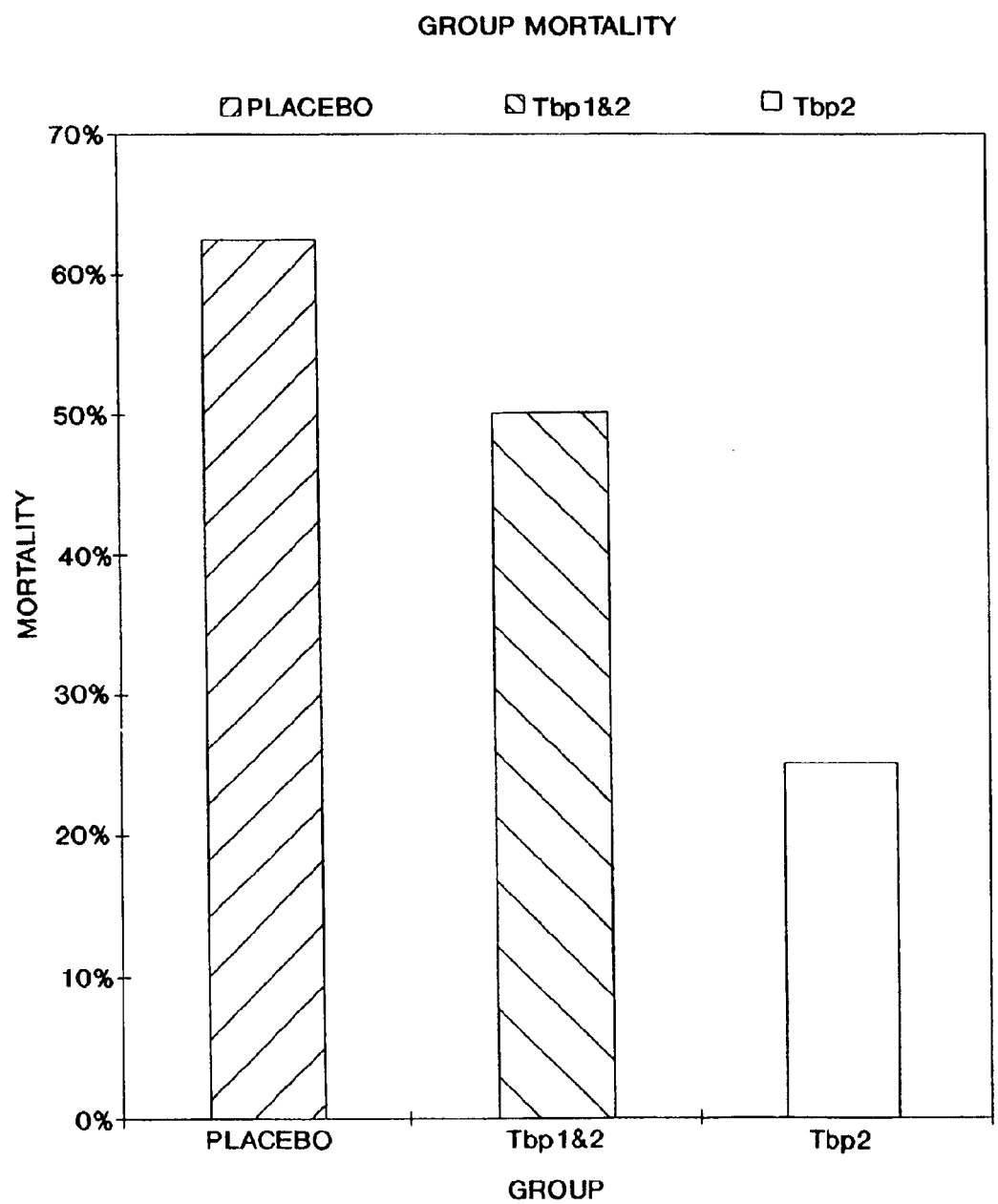

Mortality in the placebo group was 62.5%, close to an expected rate of approximately 70%. The mortality by group is shown in FIG. 7 and is listed by day in Table 1. As can be seen, immunization with vaccines containing recombinant Tbp2 reduced mortality to 25% while immunization with vaccines including a combination of Tbp1 and Tbp2, had little effect compared to the placebo. Necropsies were performed on all animals which died during the trial and in all cases, *H. somnus* was cultured from the lungs and the pathology observed was consistent with *H. somnus* pneumonia.

Since the ELISA titers to Tbp2 were similar in both of the experimental vaccine groups, it is surprising that equivalent levels of protection were not observed. However, this may simply reflect more efficient uptake of *H. somnus* by phagocytic cells in the Tbp1+Tbp2 group, allowing for increased multiplication of the bacteria in an intracellular environment.

Figure 8:
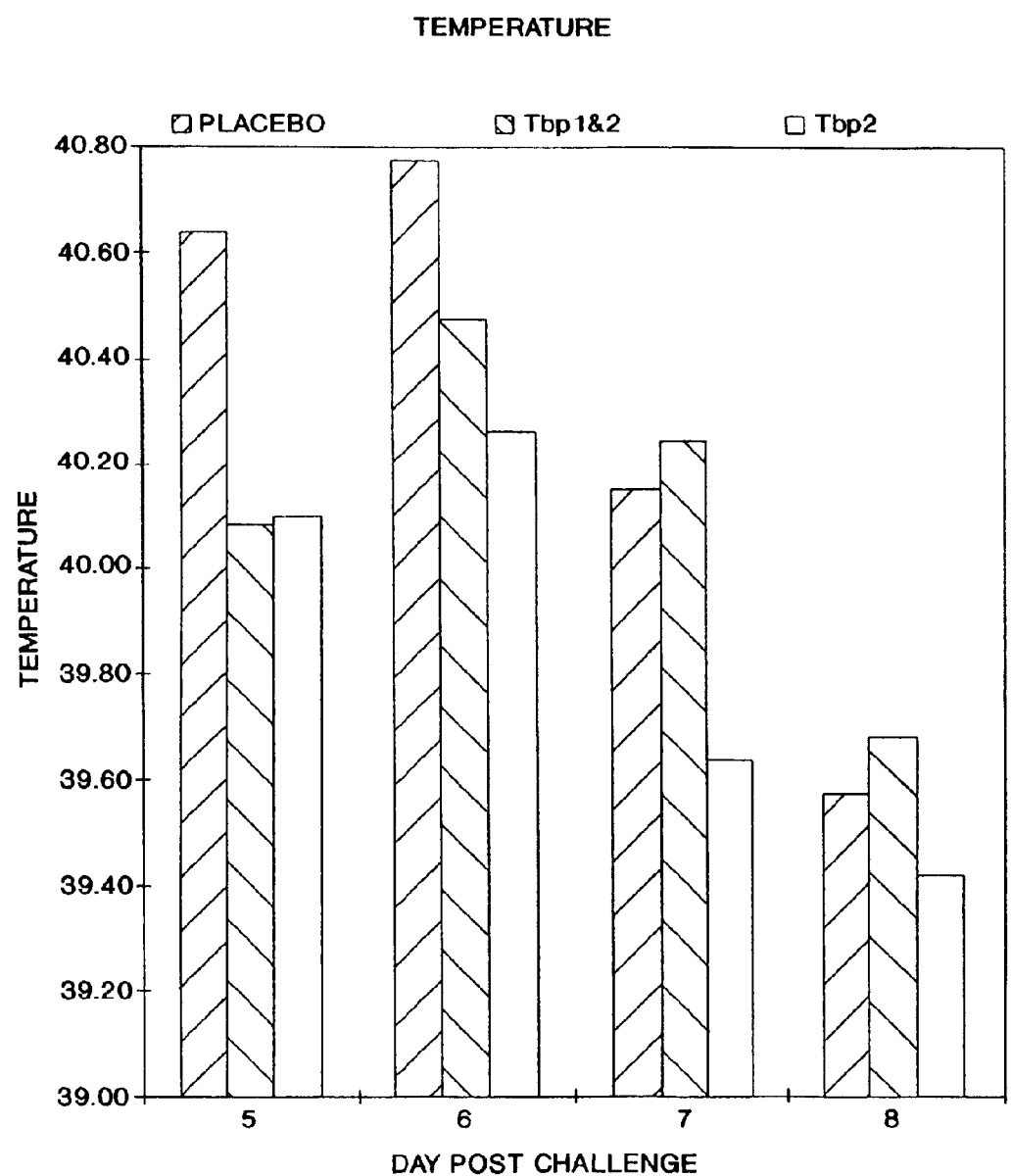
Figure 9:
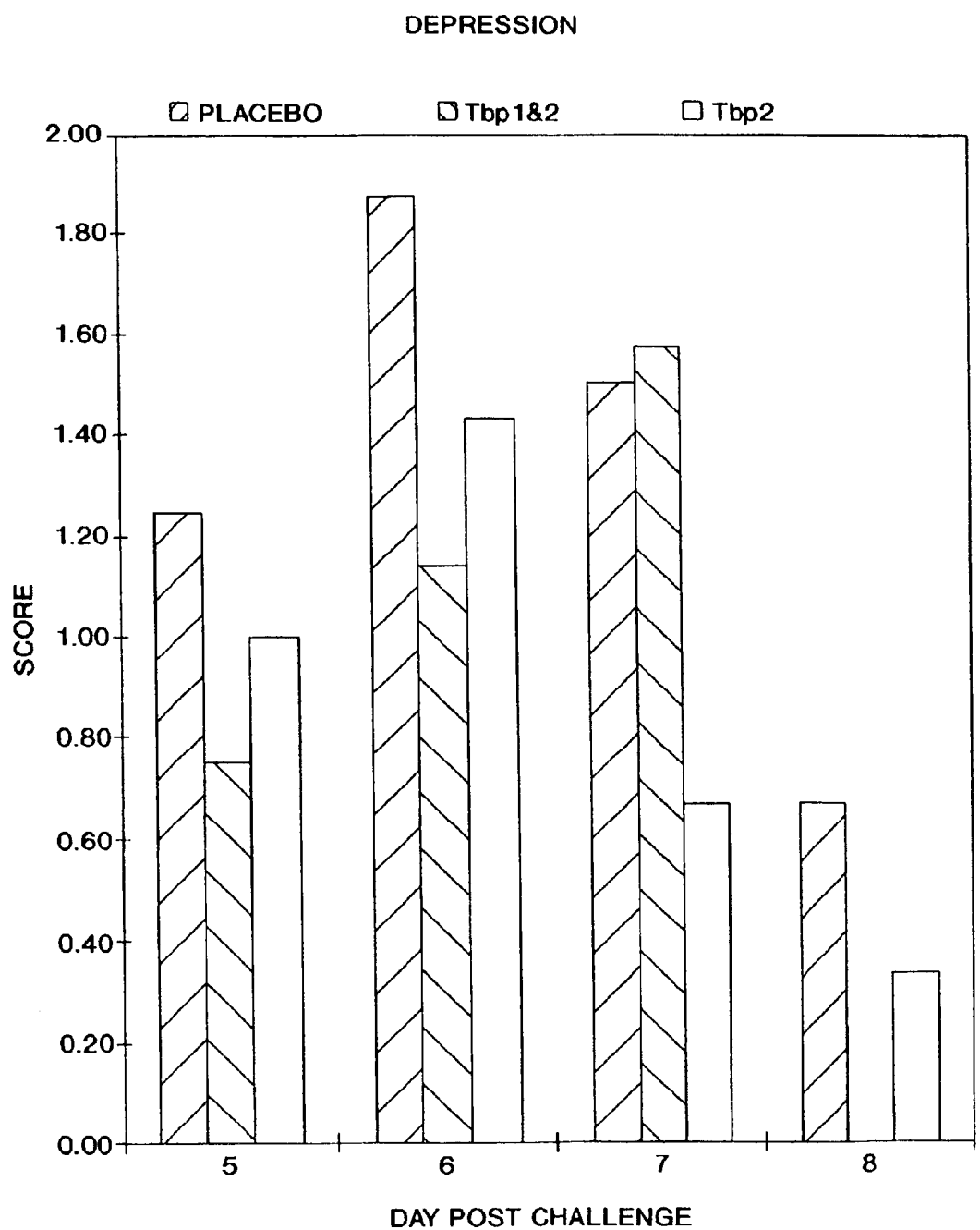
Figure 10:
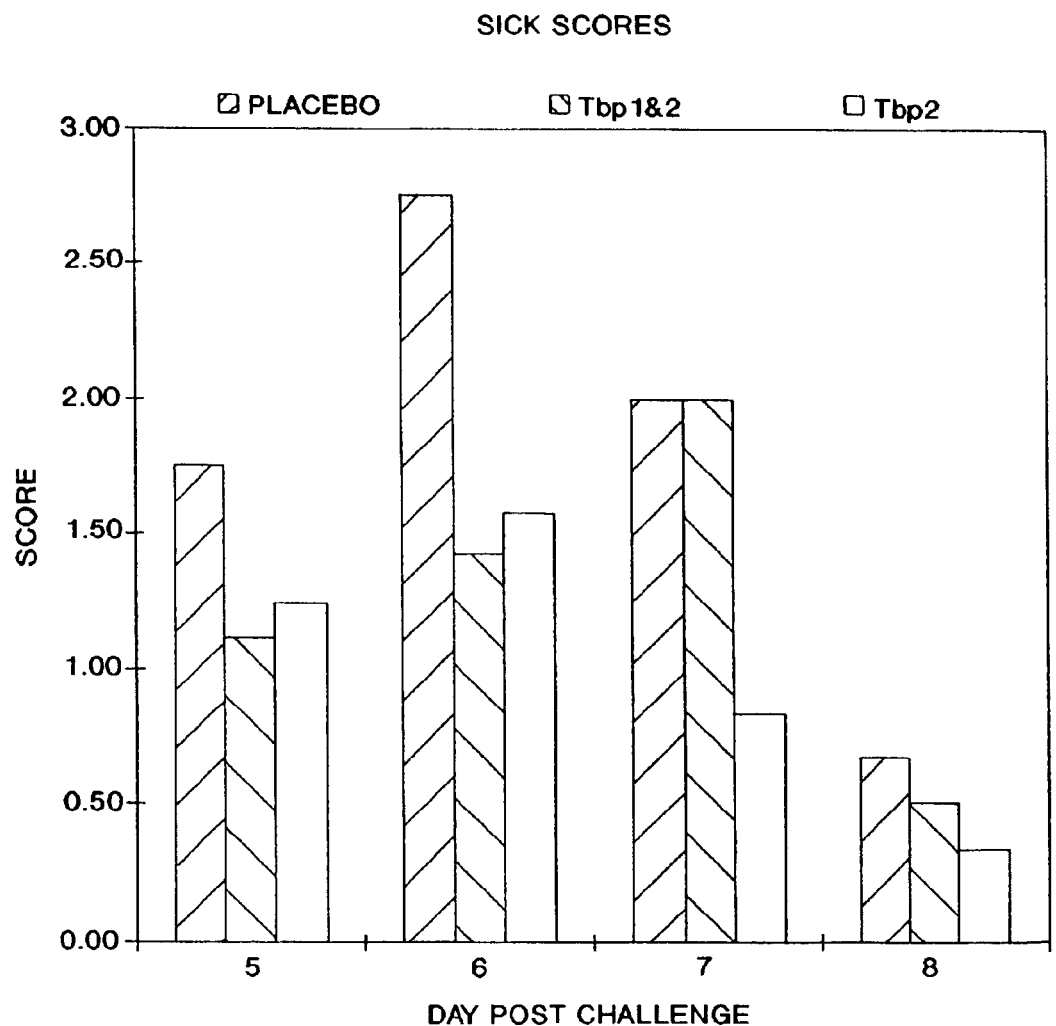

The clinical results are summarized in Table 1 and the results for temperature, depression, and sick scores are illustrated in FIGS. 8, 9 and 10, respectively. These results are similar to those obtained for mortality, with the Tbp2-immunized group showing consistently lower scores in virtually all categories. The results shown in FIGS. 8, 9 and 10 only include days 5 through 8 of the trial since animals were challenged with *H. somnus* on day 4. The clinical scores were virtually identical between all three groups on days 1 through 4.

TABLE 1

Mean clinical scores and mortality by group.

| Group | Day | Weight | Temp. | Nasal | Dep. | Str. | Resp. | Sick | Cumulative Mortality |
|---|---|---|---|---|---|---|---|---|---|
| Placebo | 0 | 259 | 38.96 | 0.00 | 0.00 | 0.00 | 0.00 | 0.00 | 0 |
| Placebo | 1 | 258 | 39.13 | 0.00 | 0.00 | 0.00 | 0.00 | 0.00 | 0 |
| Placebo | 2 | 250 | 40.94 | 0.88 | 0.38 | 0.00 | 0.00 | 1.00 | 0 |
| Placebo | 3 | 248 | 41.64 | 1.25 | 0.63 | 0.00 | 0.00 | 1.38 | 0 |
| Placebo | 4 | 244 | 40.53 | 1.75 | 0.88 | 0.00 | 0.38 | 1.25 | 0 |
| Placebo | 5 | 239 | 40.64 | 2.38 | 1.25 | 1.00 | 0.88 | 1.75 | 0 |
| Placebo | 6 | 237 | 40.77 | 2.88 | 1.88 | 1.88 | 2.00 | 2.75 | 3 |
| Placebo | 7 | 251 | 40.15 | 2.50 | 1.50 | 1.25 | 1.25 | 2.00 | 5 |
| Placebo | 8 | 259 | 39.57 | 1.33 | 0.67 | 0.33 | 0.33 | 0.67 | 5 |
| Tbp2 | 0 | 274 | 39.01 | 0.06 | 0.00 | 0.00 | 0.00 | 0.00 | 0 |
| Tbp2 | 1 | 268 | 39.19 | 0.13 | 0.00 | 0.00 | 0.00 | 0.00 | 0 |
| Tbp2 | 2 | 262 | 41.05 | 1.25 | 0.13 | 0.00 | 0.00 | 1.00 | 0 |
| Tbp2 | 3 | 257 | 41.06 | 1.13 | 0.38 | 0.00 | 0.00 | 1.00 | 0 |
| Tbp2 | 4 | 253 | 40.68 | 1.63 | 0.75 | 0.00 | 0.75 | 1.25 | 0 |
| Tbp2 | 5 | 250 | 40.10 | 1.25 | 1.00 | 0.63 | 0.50 | 1.25 | 1 |
| Tbp2 | 6 | 246 | 40.26 | 2.00 | 1.43 | 1.00 | 1.29 | 1.57 | 1 |
| Tbp2 | 7 | 254 | 39.63 | 1.33 | 0.67 | 0.33 | 0.50 | 0.83 | 2 |
| Tbp2 | 8 | 253 | 39.42 | 0.50 | 0.33 | 0.33 | 0.17 | 0.33 | 2 |
| Tbp1 + Tbp2 | 0 | 259 | 38.95 | 0.00 | 0.00 | 0.00 | 0.00 | 0.00 | 0 |
| Tbp1 + Tbp2 | 1 | 251 | 39.16 | 0.00 | 0.00 | 0.00 | 0.00 | 0.00 | 0 |
| Tbp1 + Tbp2 | 2 | 244 | 40.70 | 0.75 | 0.13 | 0.00 | 0.00 | 0.88 | 0 |
| Tbp1 + Tbp2 | 3 | 241 | 41.39 | 1.25 | 0.38 | 0.00 | 0.00 | 1.13 | 0 |
| Tbp1 + Tbp2 | 4 | 241 | 40.43 | 1.50 | 0.75 | 0.00 | 0.38 | 1.25 | 0 |
| Tbp1 + Tbp2 | 5 | 235 | 40.09 | 1.63 | 0.75 | 0.38 | 0.38 | 1.13 | 0 |
| Tbp1 + Tbp2 | 6 | 236 | 40.47 | 2.00 | 1.14 | 0.71 | 1.00 | 1.43 | 1 |
| Tbp1 + Tbp2 | 7 | 235 | 40.24 | 2.00 | 1.57 | 1.14 | 1.57 | 2.00 | 3 |
| Tbp1 + Tbp2 | 8 | 249 | 39.68 | 0.75 | 0.00 | 0.00 | 0.00 | 0.50 | 4 |

Deposits of Strains Useful in Practicing the Invention

A deposit of biologically pure cultures of the following strains was made with the American Type Culture Collection, 10801 University Boulevard, Manassas. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit. The organisms will be made available by the ATCC under the terms of the Budapest Treaty, which assures permanent and unrestricted availability of the progeny to one determined by the U.S. Commissioner of Patents and Trademarks to be entitled thereto according to 35 U.S.C. §122 and the Commissioner's rules pursuant thereto (including 37 C.F.R. §1.12 with particular reference to 886 OG 638). Upon the granting of a patent, all restrictions on the availability to the public of the deposited cultures will be irrevocably removed.

These deposits are provided merely as convenience to those of skill in the art, and are not an admission that a deposit is required under 35 U.S.C. §112. The nucleic acid sequences of these genes, as well as the amino acid sequences of the molecules encoded thereby, are incorporated herein by reference and are controlling in the event of any conflict with the description herein.

| Strain | Deposit Date | ATCC No. |
|---|---|---|
| pCRR41 in *E. coli* DH5alphaF'IQ | Jul. 14, 1998 | 98810 |
| pCRR90 in *E. coli* DH5alphaF'IQ | Jul. 14, 1998 | 98811 |

Thus, the cloning, expression and characterization of *H. somnus* transferrin-binding proteins are disclosed, as are methods of using the same. Although preferred embodiments of the subject invention have been described in some detail, it is understood that obvious variations can be made without departing from the spirit and the scope of the invention as defined by the appended claims.

What is claimed is:

1. An isolated nucleic acid molecule comprising a coding sequence for an immunogenic *H. somnus* transferrin-binding protein selected from the group consisting of (a) an immunogenic *H. somnus* transferrin-binding protein having at least 90% sequence identity to the contiguous sequence of amino acids shown at amino acid positions 1–971, inclusive, of FIG. 3 (SEQ ID NO:2); (b) an immunogenic *H. somnus* transferrin-binding protein having at least 90% sequence identity to the contiguous sequence of amino acids shown at amino acid positions 29–971, inclusive, of FIG. 3 (SEQ ID NO:2), (c) an immunogenic *H. somnus* transferrin-binding protein having at least 90% sequence identity to the contiguous sequence of amino acids shown at amino acid positions 1–662, inclusive, of FIG. 4 (SEQ ID NO:3), and (d) an immunogenic *H. somnus* transferrin-binding protein having at least 90% sequence identity to the contiguous sequence of amino acids shown at amino acid positions 20–662, inclusive, of FIG. 4 (SEQ ID NO:3).

2. The nucleic acid molecule of claim 1 wherein said molecule comprises a nucleotide sequence encoding an immunogenic transferrin-binding protein that comprises the amino acid sequence shown at amino acid positions 1–971, inclusive, of FIG. 3 (SEQ ID NO:2).

3. The nucleic acid molecule of claim 1 wherein said molecule comprises a nucleotide sequence encoding an immunogenic transferrin-binding protein that comprises the amino acid sequence shown at amino acid positions 29–971, inclusive, of FIG. 3 (SEQ ID NO:2).

4. The nucleic acid molecule of claim 1 wherein said molecule comprises a nucleotide sequence encoding an immunogenic transferrin-binding protein that comprises the amino acid sequence shown at amino acid positions 1–662, inclusive, of FIG. 4 (SEQ ID NO:3).

5. The nucleic acid molecule of claim 1 wherein said molecule comprises a nucleotide sequence encoding an immunogenic transferrin-binding protein comprises the amino acid sequence shown at amino acid positions 20–662, inclusive, of FIG. 4 (SEQ ID NO:3).

6. A recombinant vector comprising:

(a) a nucleic acid molecule according to claim 1; and (b) control elements that are operably linked to said nucleic acid molecule whereby said coding sequence can be transcribed and translated in a host cell, and at least one of said control elements is heterologous to said coding sequence.

7. A recombinant vector comprising:

(a) a nucleic acid molecule according to claim 2; and (b) control elements that are operably linked to said nucleic acid molecule whereby said coding sequence can be transcribed and translated in a host cell, and at least one of said control elements is heterologous to said coding sequence.

8. A recombinant vector comprising:

(a) a nucleic acid molecule according to claim 3; and (b) control elements that are operably linked to said nucleic acid molecule whereby said coding sequence can be transcribed and translated in a host cell, and at least one of said control elements is heterologous to said coding sequence.

9. A recombinant vector comprising:

(a) a nucleic acid molecule according to claim 4; and (b) control elements that are operably linked to said nucleic acid molecule whereby said coding sequence can be transcribed and translated in a host cell, and at least one of said control elements is heterologous to said coding sequence.

10. A recombinant vector comprising:

(a) a nucleic acid molecule according to claim 5; and (b) control elements that are operably linked to said nucleic acid molecule whereby said coding sequence can be transcribed and translated in a host cell, and at least one of said control elements is heterologous to said coding sequence.

11. A host cell transformed with the recombinant vector of claim 6.

12. A host cell transformed with the recombinant vector of claim 7.

13. A host cell transformed with the recombinant vector of claim 8.

14. A host cell transformed with the recombinant vector of claim 9.

15. A host cell transformed with the recombinant vector of claim 10.

16. A method of producing a recombinant *H. somnus* transferrin-binding protein comprising:

(a) providing a population of host cells according to claim 11; and (b) culturing said population of cells under conditions whereby the transferrin-binding protein encoded by the coding sequence present in said recombinant vector is expressed.

17. A method of producing a recombinant *H. somnus* transferrin-binding protein comprising:

(a) providing a population of host cells according to claim 12; and (b) culturing said population of cells under conditions whereby the transferrin-binding protein encoded by the coding sequence present in said recombinant vector is expressed.

18. A method of producing a recombinant *H. somnus* transferrin-binding protein comprising:

(a) providing a population of host cells according to claim 13; and (b) culturing said population of cells under conditions whereby the transferrin-binding protein encoded by the coding sequence present in said recombinant vector is expressed.

19. A method of producing a recombinant *H. somnus* transferrin-binding protein comprising:

(a) providing a population of host cells according to claim 14; and (b) culturing said population of cells under conditions whereby the transferrin-binding protein encoded by the coding sequence present in said recombinant vector is expressed.

20. A method of producing a recombinant *H. somnus* transferrin-binding protein comprising:

(a) providing a population of host cells according to claim 15; and (b) culturing said population of cells under conditions whereby the transferrin-binding protein encoded by the coding sequence present in said recombinant vector is expressed.

* * * * *

SEQUENCE LISTING

<160> NUMBER OF SEQ ID NOS: 5

<210> SEQ ID NO 1
<211> LENGTH: 6376
<212> TYPE: DNA
<213> ORGANISM: Haemophilus somnus -continued

<400> SEQUENCE: 1

```
aagcttgcat aattgcttca acgccttatc actataccgt aaagtgtaca tcactcaatt      60
cctaacatct tgcatacctc tgcgtgagaa taactcattg gggttttgtt gtagtcttcc     120
aaagactcac gatatactgc aaggtcatat tcatcttcga ttttttcaaa aacggcattc     180
ctgaacagtt cggatagcgt aatattattt gttttttgcat aggacttaaa taattgctcg    240
tcttgagcgt ttagtcttac tgaaatagcc atagtaaaat ttcctttcat tttgtattac    300
attgtaatac atttatacag aatttgcaat ataggtgaaa aagaaacag agattagacg      360
tggtcgacac gttgttttta actgacacgt tcatttggtt ttcgtgacaa atatcgcag     420
agaagttttt acggcacgat tagataaaaa attaaattta agagaaaat ctcgcaaggt      480
aaaaaccgtc agctaacgtt gttggaaatg attgcccgcc ctcagatcga ccaaaatcgc    540
acgtcttaat cgttccgagt gctgtatcgt tacaacaaac agcggctgtt taaggaatcc    600
atcagcagcg tgggcgtgtt gaaaactgta tgcattcctt aaaaaaatac atataataat    660
aattttatt tgcatatttt atataatata agaaggata taggtaaatg acctctttca       720
aattattagg cttttcggtc ttgagtgtgg ctttgctctc tgcctgctct tccggcaaag    780
gtggctttga tttagacgac gtcgagcata ccccccccctc ctcctcgggt agttcccgcc   840
ccacttatca agatgttccg actggacaac ggcagcaaga aatagtagaa gaaatcaact    900
cacctgctct aggttatgcg acagaaattc cgcgtaggaa tatttcgcca atgcccacca    960
cgggcacaaa agaaagtaat gctcgtgttg ccattactgc ccagcaagtt gcccctctta  1020
gcatgccttt taattcaata aaagaagatt ttatcaaaag gctaatagca gaaaacacca  1080
agaaaaatgc acgaggtaga gatgtaaaat attttgatga tacagatgac gtgttgtttg  1140
cacatgatgg atctaattta gcgcataaac gtgatttaca atatgttcga gttgggtatg  1200
tgttgggtac ccgaaagatt gaacttgttt tttcccatga taaaaaaaca agagatcaat  1260
ttcctgctgg ttgggtaggt tatgtttttt accaaggcac tagccctgcg gttacattac  1320
ctacacaaac cgtaacatac aaaggctatt gggattttgt tagtgatgcc ttcaatgaac  1380
gaactttagc tgaagatttt acacaggaaa atagttctgc tactagcaat ataccgggca  1440
atcaaatcgg tgcgacttca atggatgcat tggttaatcg caaagtttca ggagaaaaaa  1500
tcaatattgc tcacagtgct gagtttactg ctgattttgg cagtaaaaaa ctttcaggtg  1560
aattaaaaag taacggttat gtttctagaa tagaaaatga gcaacaagat gtaaaaacac  1620
gctacaaaat tgatgctgat atcaaaggca accgttttgt cggttcagca acagcacaag  1680
aaaaaagtca caccatcttc ggcaaggatg cggacaaacg tctcgagggc ggtttctttg  1740
gtcctaaagc cgaggaactg gcaggtaaat ttctgaccga tgataattcc ctgtttgtcg  1800
tcttttggtgc aaaacgtgaa agtaaaggcg atgaaaaact agaaacccgc tttgatgccg  1860
ttaaaatcag cacggatagt aataaattag aaaagaaac gatggatacg ttcggcaatg    1920
cggcgtattt agtgttggac ggcagacagt ttccttttggt gccggaaagt aatgccggta  1980
cgacgggcgc tggcaacaca ggcaagaatg agtttatcag caccatagac ggtagccatt  2040
taaacaaaac aaatcatgaa accacaaaa aatacaaagt taccgtatgt tgcagtaatt   2100
tggtgtatgt gaaattcggc agctatgggg aacaaacaac agcaaacgat gcttcaaaca  2160
gcactgccgg tgcagcaact acgcataaca gcacattaac aaacggacac cttttcctaa  2220
caggtgaacg tacttcgctt actgatatgg cgaagcaaag tggtgcagca aagtatattg  2280
gcacatggca agccaacttt ttaagtagca aaggacaggt tggcagtgtt gacgccggtg  2340
```

```
atccgcgtaa cgatagtggt aaaagccgtg ctgaatttga tgttaatttt ggtggtaaga    2400
cagttacagg caagttttt gatgccgacg gtattcaacc cgccctcaca atggatagta    2460
ccaagattga aggtaacggc ttctcgggta cagctaagac aactggtagt ttgcaattag    2520
ataaaggcag tacaggtgcg ggtataacag taaccttcac cgatgctaaa gtcgatggcg    2580
cattctacgg tccgaatgca gaagaaatcg gcggtaccat cacatcgaat ggcacgggcg    2640
ataaagtcgg tggggtgttc ggtgcgaaac gccaagaact atcgcaacag aaatgaaatc    2700
ttaactctag ctacctgaaa catatttcag gtagcaggat gggtatctgc tgatatgctc    2760
aacctgcttg aaaaagtttg tcaaatccgc cgcctgtcgt tgttgacggt gtgatgttgc    2820
agtggcaaat cgctcggctt tgttgagaaa gcatgaccca tccgtctttt actcacacgg    2880
aacgaaaaaa atgtctacaa aacctttgtt taaacttaag ctgataacat ggctgtcag    2940
cacgatttt ttaccttta ctgaggcggt tgccgatact gaatcaccga gtagcaatac    3000
agaagcagtg ctggagttag aagctatcca ggtgcaagcc aaacacgaga tcagcagaca    3060
tgacaatgaa gtcaccggtt tgggtaaggt ggtcaaaagc agtgaagaca ttgataaaga    3120
actgattttg aatattcgcg atttgacccg ttatgatccc ggtatttcgg tggtggagca    3180
gggacgtggt gcaacgtcag gctatgcaat gcgtggtgtt gacagaaacc gcgtggctat    3240
gttggtggac ggcttgggac aggcgcagtc ctattctacc ttgaaatccg atgccaacgg    3300
cggggcgatt aatgaaattg aatatgagaa tattaaatca attgaattga gcaaggggtc    3360
cagttcggca gaatacggta gcggtgcctt gggcggtgcg gtagggtttc gtaccaaaga    3420
agctgatgat gtgattaaag aggggcaaaa ctggggcttg aacagtaaaa cggcttacag    3480
cagcaaaaac agccagttta cccaatccgt tgccggtgcg ttccgtgtcg gcggttttga    3540
cagtttggcg attttaccc atcgtaaagg taaggaaacc cgcgtgcatc ctgctgccga    3600
agaaatacaa catacttacc aaccattgga agggtatttt aatcggtatg aggttgacca    3660
aaaccgcaac ggaaagcctg ttctggcgaa tgcgtattat atacttgccg atgaatgctc    3720
taatctaagt gatccgagtt gtcgtcatgc caaggccaag acgaataggg tgggtgcccc    3780
ggagaacaat cctaattgga cgcccgaaga gcaggcacag gctgctaaaa tgccgtatcc    3840
gacacgtacc gcctctgcca aagattatac gggtcctgac cgcatcagcc ctaatccgat    3900
ggactaccaa agtcactctt tcttctggaa aggtggttac cgcttgtcgc ctaaccatta    3960
tgtcggcggg gtgttggaac atacgaagca gcgttacgat atccgtgata tgacgcaacg    4020
ggcgtattac acgaaagagg atatctgcca cagcggatcc agttgccaaa cgttggataa    4080
aaatgagacg gacaaaggta atttcggtat cacgttgact gataatcctt tggacggttt    4140
ggtatatgat gccggcaatc aagctcgtgg cgtgcggtac ggacggggta aatttttaa    4200
tgaacgccat acgaaaaatc gctcgggtat cttttaccgc tatgagaatc ccgataaaaa    4260
ttcttggcca gatagcttga ccttgagtat tgaccgccaa gatctcaaac tgtcgagccg    4320
tatccattgg acgtattgca ccgattatcc tcatgtggca cgttgccgtg ccagcttgga    4380
caaaccttgg tctaattacc gtaccgagaa aaacgattat caagaacgac tcaatctggg    4440
acaattcaat tgggaaaaaa ctttaatct gggcttacc acgcataagg tgaatatcgc    4500
cgccggcttt ggtacacatc gctccacctt acaacatggc gacttatatg ctgaatatgt    4560
caccttgcca ccgtatacag aggaaaaagt gtatggcgaa gataataagg tcaaacaaaa    4620
tccgacagca gaagaaaaag agaaattaca atacggcaat ggttcttatg acaaacctcg    4680
```

-continued

```
cgtatataga cgtaaaaaca cgccggaatt aaaaactgtc aatgggtgca atgagacagc   4740
aggcgataac cgtgactgct cgccacgtgt gattacgggc agacagtatt accttgcctt   4800
gcgtaaccat attgcctttg gtgaatgggc agacttgggg ttgggcgtgc ggtacgacaa   4860
ccatacccttc cgctcgaatg acccgtggac caaaggtgga aactaccaca actggtcgtg   4920
gaatgcgggc gtgagcctca aaccaacccg ccactttgtc gtgtcttacc gtgtgtccag   4980
cggtttccgt gtccccgctt tttatgagct gtacggcgtg cgtacggggg cttctggtaa   5040
agacaatcca ctcacacaaa aagagttctt gagccgtaaa ccgttgaaaa gcgaaaaagc   5100
ctttaaccaa gaaattggtt tggccgttca gggcgatttt ggtgtgatag agaccagttt   5160
cttccaaaac aactataaaa acctgcttgc ccgtgcagat aaatatgtcg agggattggg   5220
ttatgtaacc gatttttaca acacccaaga tgtcaaactc aacggtatca atatcttggg   5280
tagaatctac tgggaaggca tcagcgatag gctgcctgaa ggcttgtatt ccacacttgc   5340
ttacaaccgt atcaatatca aagcacgcaa attgcacgac aattttacca atgtgtctga   5400
gccgacattg gaagcagtgc aaccgggacg cattattgca agtatcggct atgatgaccc   5460
tgagggcaga tggggcctta atttaagcgg cacctactct caagccaaac aacgtgacga   5520
agtggtcggc gaaaaagtgt tcggcaaggg tggcagcatt aaacggacga tcaacagcaa   5580
acgcactcgt gcttggtata tttatgattt gacggcatac tacacttgga agaaaaatt   5640
cacgttgaga gccggtatct ataatttaac caatcgtaaa tatagcacat gggaaagtgt   5700
gcgtcagtcc gctgccaatg cggtcaatca agacctaggt acacgttcgg cacgttttgc   5760
cgcacggggc agaaacttta ccgtgagtat ggaaatgaag ttttaattaa aaaactgtct   5820
gcaagctgtt taaaaacag ttaagatgat ttgttcgtat aaatagctgc ctgaagtctt   5880
gttatgcagg ttcaggcagc ttgacattac aaaaaaagga aaaagtcta atggaagaca   5940
aatatgctat ttgtcggcaa cgaaaaattg ttgcaatgga ttagcagttc aagtggcttc   6000
cggtattttt tatcgcactt tttctatcta taagcttgaa atctttattt ccgaacttat   6060
attttcgctg tttgttaatt tcactattgg aaaaggaaat attatgtcaa caaatcaaga   6120
aacacgtggt tttcagtctg aagttaaaca gcttttacaa ttgatgattc attctctta   6180
ttcaaataaa gagatttttt tgcgtgagtt gatttccaat gcgtctgatg cggcggataa   6240
attgcgtttt aaagccttgt ctgcacctga attatatgaa ggagatggtg atttaaaagt   6300
gcggatcagt tttgacgcag agaaaggtac gttaaccatt agcgataatg gtattggtat   6360
gacgagagag caggtg                                                   6376
```

<210> SEQ ID NO 2
<211> LENGTH: 971
<212> TYPE: PRT
<213> ORGANISM: Haemophilus somnus

<400> SEQUENCE: 2

```
Met Ser Thr Lys Pro Leu Phe Lys Leu Lys Leu Ile Thr Leu Ala Val
 1               5                  10                  15

Ser Thr Ile Phe Leu Pro Phe Thr Glu Ala Val Ala Asp Thr Glu Ser
            20                  25                  30

Pro Ser Ser Asn Thr Glu Ala Val Leu Glu Leu Glu Ala Ile Gln Val
        35                  40                  45

Gln Ala Lys His Glu Ile Ser Arg His Asp Asn Glu Val Thr Gly Leu
    50                  55                  60

Gly Lys Val Val Lys Ser Ser Glu Asp Ile Asp Lys Glu Leu Ile Leu
```

-continued

```
                65                  70                  75                  80
Asn Ile Arg Asp Leu Thr Arg Tyr Asp Pro Gly Ile Ser Val Val Glu
                    85                  90                  95
Gln Gly Arg Gly Ala Thr Ser Gly Tyr Ala Met Arg Gly Val Asp Arg
                100                 105                 110
Asn Arg Val Ala Met Leu Val Asp Gly Leu Gly Gln Ala Gln Ser Tyr
                115                 120                 125
Ser Thr Leu Lys Ser Asp Ala Asn Gly Gly Ala Ile Asn Glu Ile Glu
    130                 135                 140
Tyr Glu Asn Ile Lys Ser Ile Glu Leu Ser Lys Gly Ser Ser Ser Ala
145                 150                 155                 160
Glu Tyr Gly Ser Gly Ala Leu Gly Gly Ala Val Gly Phe Arg Thr Lys
                165                 170                 175
Glu Ala Asp Asp Val Ile Lys Glu Gly Gln Asn Trp Gly Leu Asn Ser
                180                 185                 190
Lys Thr Ala Tyr Ser Ser Lys Asn Ser Gln Phe Thr Gln Ser Val Ala
                195                 200                 205
Gly Ala Phe Arg Val Gly Gly Phe Asp Ser Leu Ala Ile Phe Thr His
    210                 215                 220
Arg Lys Gly Lys Glu Thr Arg Val His Pro Ala Ala Glu Glu Ile Gln
225                 230                 235                 240
His Thr Tyr Gln Pro Leu Glu Gly Tyr Phe Asn Arg Tyr Glu Val Asp
                245                 250                 255
Gln Asn Arg Asn Gly Lys Pro Val Leu Ala Asn Ala Tyr Tyr Ile Leu
                260                 265                 270
Ala Asp Glu Cys Ser Asn Leu Ser Asp Pro Ser Cys Arg His Ala Lys
    275                 280                 285
Ala Lys Thr Asn Arg Val Gly Ala Pro Glu Asn Asn Pro Asn Trp Thr
    290                 295                 300
Pro Glu Glu Gln Ala Gln Ala Ala Lys Met Pro Tyr Pro Thr Arg Thr
305                 310                 315                 320
Ala Ser Ala Lys Asp Tyr Thr Gly Pro Asp Arg Ile Ser Pro Asn Pro
                325                 330                 335
Met Asp Tyr Gln Ser His Ser Phe Phe Trp Lys Gly Tyr Arg Leu
                340                 345                 350
Ser Pro Asn His Tyr Val Gly Gly Val Leu Glu His Thr Lys Gln Arg
    355                 360                 365
Tyr Asp Ile Arg Asp Met Thr Gln Arg Ala Tyr Tyr Thr Lys Glu Asp
    370                 375                 380
Ile Cys His Ser Gly Ser Ser Cys Gln Thr Leu Asp Lys Asn Glu Thr
385                 390                 395                 400
Asp Lys Gly Asn Phe Gly Ile Thr Leu Thr Asp Asn Pro Leu Asp Gly
                405                 410                 415
Leu Val Tyr Asp Ala Gly Asn Gln Ala Arg Gly Val Arg Tyr Gly Arg
                420                 425                 430
Gly Lys Phe Phe Asn Glu Arg His Thr Lys Asn Arg Ser Gly Ile Phe
    435                 440                 445
Tyr Arg Tyr Glu Asn Pro Asp Lys Asn Ser Trp Pro Asp Ser Leu Thr
    450                 455                 460
Leu Ser Ile Asp Arg Gln Asp Leu Lys Leu Ser Ser Arg Ile His Trp
465                 470                 475                 480
Thr Tyr Cys Thr Asp Tyr Pro His Val Ala Arg Cys Arg Ala Ser Leu
                485                 490                 495
```

```
Asp Lys Pro Trp Ser Asn Tyr Arg Thr Glu Lys Asn Asp Tyr Gln Glu
            500                 505                 510

Arg Leu Asn Leu Gly Gln Phe Asn Trp Glu Lys Thr Phe Asn Leu Gly
            515                 520                 525

Phe Thr Thr His Lys Val Asn Ile Ala Ala Gly Phe Gly Thr His Arg
            530                 535             540

Ser Thr Leu Gln His Gly Asp Leu Tyr Ala Glu Tyr Val Thr Leu Pro
545                 550                 555                 560

Pro Tyr Thr Glu Lys Val Tyr Gly Glu Asp Asn Lys Val Lys Gln
                565                 570                 575

Asn Pro Thr Ala Glu Glu Lys Glu Lys Leu Gln Tyr Gly Asn Gly Ser
            580                 585                 590

Tyr Asp Lys Pro Arg Val Tyr Arg Lys Asn Thr Pro Glu Leu Lys
            595                 600                 605

Thr Val Asn Gly Cys Asn Glu Thr Ala Gly Asp Asn Arg Asp Cys Ser
            610                 615                 620

Pro Arg Val Ile Thr Gly Arg Gln Tyr Tyr Leu Ala Leu Arg Asn His
625                 630                 635                 640

Ile Ala Phe Gly Glu Trp Ala Asp Leu Gly Leu Gly Val Arg Tyr Asp
                645                 650                 655

Asn His Thr Phe Arg Ser Asn Asp Pro Trp Thr Lys Gly Gly Asn Tyr
                660                 665                 670

His Asn Trp Ser Trp Asn Ala Gly Val Ser Leu Lys Pro Thr Arg His
                675                 680                 685

Phe Val Val Ser Tyr Arg Val Ser Ser Gly Phe Arg Val Pro Ala Phe
            690                 695                 700

Tyr Glu Leu Tyr Gly Val Arg Thr Gly Ala Ser Gly Lys Asp Asn Pro
705                 710                 715                 720

Leu Thr Gln Lys Glu Phe Leu Ser Arg Lys Pro Leu Lys Ser Glu Lys
                725                 730                 735

Ala Phe Asn Gln Glu Ile Gly Leu Ala Val Gln Gly Asp Phe Gly Val
            740                 745                 750

Ile Glu Thr Ser Phe Phe Gln Asn Asn Tyr Lys Asn Leu Leu Ala Arg
            755                 760                 765

Ala Asp Lys Tyr Val Glu Gly Leu Gly Tyr Val Thr Asp Phe Tyr Asn
            770                 775                 780

Thr Gln Asp Val Lys Leu Asn Gly Ile Asn Ile Leu Gly Arg Ile Tyr
785                 790                 795                 800

Trp Glu Gly Ile Ser Asp Arg Leu Pro Glu Gly Leu Tyr Ser Thr Leu
                805                 810                 815

Ala Tyr Asn Arg Ile Asn Ile Lys Ala Arg Lys Leu His Asp Asn Phe
            820                 825                 830

Thr Asn Val Ser Glu Pro Thr Leu Glu Ala Val Gln Pro Gly Arg Ile
            835                 840                 845

Ile Ala Ser Ile Gly Tyr Asp Asp Pro Glu Gly Arg Trp Gly Leu Asn
850                 855                 860

Leu Ser Gly Thr Tyr Ser Gln Ala Lys Gln Arg Asp Glu Val Val Gly
865                 870                 875                 880

Glu Lys Val Phe Gly Lys Gly Ser Ile Lys Arg Thr Ile Asn Ser
                885                 890                 895

Lys Arg Thr Arg Ala Trp Tyr Ile Tyr Asp Leu Thr Ala Tyr Tyr Thr
            900                 905                 910
```

```
Trp Lys Glu Lys Phe Thr Leu Arg Ala Gly Ile Tyr Asn Leu Thr Asn
            915                 920                 925

Arg Lys Tyr Ser Thr Trp Glu Ser Val Arg Gln Ser Ala Ala Asn Ala
        930                 935                 940

Val Asn Gln Asp Leu Gly Thr Arg Ser Ala Arg Phe Ala Ala Arg Gly
945                 950                 955                 960

Arg Asn Phe Thr Val Ser Met Glu Met Lys Phe
            965                 970

<210> SEQ ID NO 3
<211> LENGTH: 662
<212> TYPE: PRT
<213> ORGANISM: Haemophilus somnus

<400> SEQUENCE: 3

Met Thr Ser Phe Lys Leu Leu Gly Phe Ser Val Leu Ser Val Ala Leu
  1               5                  10                  15

Leu Ser Ala Cys Ser Ser Gly Lys Gly Gly Phe Asp Leu Asp Asp Val
             20                  25                  30

Glu His Thr Pro Pro Ser Ser Ser Gly Ser Ser Arg Pro Thr Tyr Gln
         35                  40                  45

Asp Val Pro Thr Gly Gln Arg Gln Gln Glu Ile Val Glu Glu Ile Asn
     50                  55                  60

Ser Pro Ala Leu Gly Tyr Ala Thr Glu Ile Pro Arg Arg Asn Ile Ser
 65                  70                  75                  80

Pro Met Pro Thr Thr Gly Thr Lys Glu Ser Asn Ala Arg Val Ala Ile
                 85                  90                  95

Thr Ala Gln Gln Val Ala Pro Leu Ser Met Pro Phe Asn Ser Ile Lys
            100                 105                 110

Glu Asp Phe Ile Lys Arg Leu Ile Ala Glu Asn Thr Lys Lys Asn Ala
        115                 120                 125

Arg Gly Arg Asp Val Lys Tyr Phe Asp Asp Thr Asp Val Leu Phe
    130                 135                 140

Ala His Asp Gly Ser Asn Leu Ala His Lys Arg Asp Leu Gln Tyr Val
145                 150                 155                 160

Arg Val Gly Tyr Val Leu Gly Thr Arg Lys Ile Glu Leu Val Phe Ser
                165                 170                 175

His Asp Lys Lys Thr Arg Asp Gln Phe Pro Ala Gly Trp Val Gly Tyr
            180                 185                 190

Val Phe Tyr Gln Gly Thr Ser Pro Ala Val Thr Leu Pro Thr Gln Thr
        195                 200                 205

Val Thr Tyr Lys Gly Tyr Trp Asp Phe Val Ser Asp Ala Phe Asn Glu
    210                 215                 220

Arg Thr Leu Ala Glu Asp Phe Thr Gln Glu Asn Ser Ser Ala Thr Ser
225                 230                 235                 240

Asn Ile Pro Gly Asn Gln Ile Gly Ala Thr Ser Met Asp Ala Leu Val
                245                 250                 255

Asn Arg Lys Val Ser Gly Glu Lys Ile Asn Ile Ala His Ser Ala Glu
            260                 265                 270

Phe Thr Ala Asp Phe Gly Ser Lys Lys Leu Ser Gly Glu Leu Lys Ser
        275                 280                 285

Asn Gly Tyr Val Ser Arg Ile Glu Asn Glu Gln Gln Asp Val Lys Thr
    290                 295                 300

Arg Tyr Lys Ile Asp Ala Asp Ile Lys Gly Asn Arg Phe Val Gly Ser
305                 310                 315                 320
```

Ala Thr Ala Gln Glu Lys Ser His Thr Ile Phe Gly Lys Asp Ala Asp
            325                 330                 335

Lys Arg Leu Glu Gly Gly Phe Phe Gly Pro Lys Ala Glu Glu Leu Ala
        340                 345                 350

Gly Lys Phe Leu Thr Asp Asp Asn Ser Leu Phe Val Val Phe Gly Ala
    355                 360                 365

Lys Arg Glu Ser Lys Gly Asp Glu Lys Leu Glu Thr Arg Phe Asp Ala
370                 375                 380

Val Lys Ile Ser Thr Asp Ser Asn Lys Leu Glu Lys Glu Thr Met Asp
385                 390                 395                 400

Thr Phe Gly Asn Ala Ala Tyr Leu Val Leu Asp Gly Arg Gln Phe Pro
                405                 410                 415

Leu Val Pro Glu Ser Asn Ala Gly Thr Thr Gly Ala Gly Asn Thr Gly
            420                 425                 430

Lys Asn Glu Phe Ile Ser Thr Ile Asp Gly Ser His Leu Asn Lys Thr
        435                 440                 445

Asn His Glu Asn His Lys Lys Tyr Lys Val Thr Val Cys Cys Ser Asn
    450                 455                 460

Leu Val Tyr Val Lys Phe Gly Ser Tyr Gly Glu Gln Thr Thr Ala Asn
465                 470                 475                 480

Asp Ala Ser Asn Ser Thr Ala Gly Ala Ala Thr Thr His Asn Ser Thr
                485                 490                 495

Leu Thr Asn Gly His Leu Phe Leu Thr Gly Glu Arg Thr Ser Leu Thr
            500                 505                 510

Asp Met Ala Lys Gln Ser Gly Ala Ala Lys Tyr Ile Gly Thr Trp Gln
        515                 520                 525

Ala Asn Phe Leu Ser Ser Lys Gly Gln Val Gly Ser Val Asp Ala Gly
    530                 535                 540

Asp Pro Arg Asn Asp Ser Gly Lys Ser Arg Ala Glu Phe Asp Val Asn
545                 550                 555                 560

Phe Gly Gly Lys Thr Val Thr Gly Lys Phe Phe Asp Ala Asp Gly Ile
                565                 570                 575

Gln Pro Ala Leu Thr Met Asp Ser Thr Lys Ile Glu Gly Asn Gly Phe
            580                 585                 590

Ser Gly Thr Ala Lys Thr Thr Gly Ser Leu Gln Leu Asp Lys Gly Ser
        595                 600                 605

Thr Gly Ala Gly Ile Thr Val Thr Phe Thr Asp Ala Lys Val Asp Gly
    610                 615                 620

Ala Phe Tyr Gly Pro Asn Ala Glu Glu Ile Gly Gly Thr Ile Thr Ser
625                 630                 635                 640

Asn Gly Thr Gly Asp Lys Val Gly Gly Val Phe Gly Ala Lys Arg Gln
                645                 650                 655

Glu Leu Ser Gln Gln Lys
            660

<210> SEQ ID NO 4
<211> LENGTH: 2179
<212> TYPE: DNA
<213> ORGANISM: Haemophilus somnus
<220> FEATURE:
<221> NAME/KEY: CDS
<222> LOCATION: (872)..(1906)

<400> SEQUENCE: 4
cgacgccagt gccaagcttg catgcctgca ggtgatctaa gcttcccggg atccaagagg      60

```
                                                        -continued tgaagagatt tattggattg gaccaatagg actggcagaa atgaatcgg aaggaacgga    120 cttccatgcc gttaaaaacg gctatgtgtc aattacaccc attcaaacag atatgacggc    180
atatcattca atgacagctt tacaacaatg gttagataag gaataacgat aatcttttca    240
tcgaaggaat aaaacatgaa aattttcggt acgctatatg ataaaactat gcaatgggca    300
aatcaccgtt ttgctacatt ttggctaact tttgttagtt ttattgaggc tattttcttc    360
ccaataccac ctgatgtcat gcttattccg atgtcaataa ataaacctaa atgtgctact    420
aaatttgcat tttatgcagc aatggcttca gccattggtg gggcaattgg ttatggatta    480
ggttattacg cttttgattt catacaaagt tatattcaac aatggggtta tcaacaacat    540
tgggaaactg ctctttcttg gttcaaagaa tggggtattt gggtagtttt cgttgcaggt    600
ttttcaccta ttccttataa aattttacg atttgtgcag gcgtcatgca aatggcattt    660
ttgcctttct tacttactgc ctttattct cgtattgcaa gattttttgct cgttacccat    720 ttagcggctt ggagcggaaa aaaatttgct gcgaaattac gtcaatctat tgaatttatc    780
ggttggtcag ttgtcattat tgctatagtt gtatatcttg tcttgaaata atctaagata    840
aaaaatgaat ataaagtaac ggagaattta c atg aaa aaa ttt tta cct tta      892
                                   Met Lys Lys Phe Leu Pro Leu
                                    1               5 tct att agt atc act gta cta gct gct tgt agt tca cac act ccg gct    940
Ser Ile Ser Ile Thr Val Leu Ala Ala Cys Ser Ser His Thr Pro Ala
        10              15                  20 ccg gta gaa aat gct aag gat tta gca cca agt att atc aaa ccg att    988
Pro Val Glu Asn Ala Lys Asp Leu Ala Pro Ser Ile Ile Lys Pro Ile
    25                  30                  35 aat ggt aca aac tca acc gct tgg gaa cct caa gtt att caa caa aag   1036
Asn Gly Thr Asn Ser Thr Ala Trp Glu Pro Gln Val Ile Gln Gln Lys
40                  45                  50                  55 atg ccc gaa agt atg aga gtg ccg aaa gca aca aac tcc act tat caa   1084
Met Pro Glu Ser Met Arg Val Pro Lys Ala Thr Asn Ser Thr Tyr Gln
                60                  65                  70 cct gaa atc att caa caa aat caa caa aaa aca gaa tcg ata gca aaa   1132
Pro Glu Ile Ile Gln Gln Asn Gln Gln Lys Thr Glu Ser Ile Ala Lys
            75                  80                  85 aaa cag gct cta caa aat ttt gaa att cca aga gat cct aaa act aat   1180
Lys Gln Ala Leu Gln Asn Phe Glu Ile Pro Arg Asp Pro Lys Thr Asn
        90                  95                  100 gtg cct gtt tat agc aaa att gat aag ggt ttt tac aaa ggt gat act   1228
Val Pro Val Tyr Ser Lys Ile Asp Lys Gly Phe Tyr Lys Gly Asp Thr
    105                 110                 115 tac aaa gta cgc aaa ggc gat acc atg ttt ctt att gct tat att tca   1276
Tyr Lys Val Arg Lys Gly Asp Thr Met Phe Leu Ile Ala Tyr Ile Ser
120                 125                 130                 135 ggc atg gat ata aaa gaa ttg gcc aca cta aat aat atg tct gag cca   1324
Gly Met Asp Ile Lys Glu Leu Ala Thr Leu Asn Asn Met Ser Glu Pro
                140                 145                 150 tat cat ctg agt att gga caa gta ttg aaa att gca aat aat att ccc   1372
Tyr His Leu Ser Ile Gly Gln Val Leu Lys Ile Ala Asn Asn Ile Pro
            155                 160                 165 gat agc aat atg ata cca aca cag aca ata aat gaa tca gag gtg aca   1420
Asp Ser Asn Met Ile Pro Thr Gln Thr Ile Asn Glu Ser Glu Val Thr
        170                 175                 180 caa aat aca gtc aat gag aca tgg aat gct aat aaa cca aca aat gaa   1468
Gln Asn Thr Val Asn Glu Thr Trp Asn Ala Asn Lys Pro Thr Asn Glu
    185                 190                 195
```

-continued

```
caa atg aaa ccc gtt gct aca cca aca cat tca aca atg cca atc aat      1516
Gln Met Lys Pro Val Ala Thr Pro Thr His Ser Thr Met Pro Ile Asn
200                 205                 210                 215 aaa aca cct cca gcc acc tca aat ata gct tgg att tgg cca aca aat      1564
Lys Thr Pro Pro Ala Thr Ser Asn Ile Ala Trp Ile Trp Pro Thr Asn
                220                 225                 230 gga aaa att att caa gga ttt tcc agt gct gat gga ggc aat aaa ggt      1612
Gly Lys Ile Ile Gln Gly Phe Ser Ser Ala Asp Gly Gly Asn Lys Gly
            235                 240                 245 att gat att agc ggt tct cgt gga caa gct gtt aat gca gca gct gct      1660
Ile Asp Ile Ser Gly Ser Arg Gly Gln Ala Val Asn Ala Ala Ala Ala
        250                 255                 260 gga cga gtt gta tat gcc gga gac gct tta cgt gga tat ggt aat tta      1708
Gly Arg Val Val Tyr Ala Gly Asp Ala Leu Arg Gly Tyr Gly Asn Leu
    265                 270                 275 att att att aaa cat aat gac agt tat tta agt gct tat gca cat aat      1756
Ile Ile Ile Lys His Asn Asp Ser Tyr Leu Ser Ala Tyr Ala His Asn
280                 285                 290                 295 gaa agt ata ctc gtc aaa gat cag caa gaa gtt aaa gcg ggt caa caa      1804
Glu Ser Ile Leu Val Lys Asp Gln Gln Glu Val Lys Ala Gly Gln Gln
                300                 305                 310 att gct aaa atg gga agt tct gga aca aac aca atc aaa ctc cat ttt      1852
Ile Ala Lys Met Gly Ser Ser Gly Thr Asn Thr Ile Lys Leu His Phe
            315                 320                 325 gaa att cgt tat aaa ggt caa tca gta gat cca atg aga tat tta cca      1900
Glu Ile Arg Tyr Lys Gly Gln Ser Val Asp Pro Met Arg Tyr Leu Pro
        330                 335                 340 aaa aat taatcctaaa aaaatctgca ccttcatcag ttagttgttt agtccaactt       1956
Lys Asn
    345 ttggggtgca gatcatttca gttatcagct ttttattaac tattttttga aaattgcatt    2016 aggcaaacgt tttcgttccg ataaaaattc ctttataatg tggtcgtttt ttattttttt    2076 gatggatctt ttctatgtta cacatttttc gtggcacgcc cgcattatcc aattttcgtt    2136 taaatcagtt attcagtggt ttcagcaaga taatttaccc att                      2179
```

<210> SEQ ID NO 5
<211> LENGTH: 345
<212> TYPE: PRT
<213> ORGANISM: Haemophilus somnus

<400> SEQUENCE: 5

```
Met Lys Lys Phe Leu Pro Leu Ser Ile Ser Ile Thr Val Leu Ala Ala
1               5                   10                  15

Cys Ser Ser His Thr Pro Ala Pro Val Glu Asn Ala Lys Asp Leu Ala
            20                  25                  30

Pro Ser Ile Ile Lys Pro Ile Asn Gly Thr Asn Ser Thr Ala Trp Glu
        35                  40                  45

Pro Gln Val Ile Gln Lys Met Pro Glu Ser Met Arg Val Pro Lys
    50                  55                  60

Ala Thr Asn Ser Thr Tyr Gln Pro Glu Ile Ile Gln Asn Gln Gln
65                  70                  75                  80

Lys Thr Glu Ser Ile Ala Lys Lys Gln Ala Leu Gln Asn Phe Glu Ile
                85                  90                  95

Pro Arg Asp Pro Lys Thr Asn Val Pro Val Tyr Ser Lys Ile Asp Lys
            100                 105                 110

Gly Phe Tyr Lys Gly Asp Thr Tyr Lys Val Arg Lys Gly Asp Thr Met
        115                 120                 125
```

-continued

```
Phe Leu Ile Ala Tyr Ile Ser Gly Met Asp Ile Lys Glu Leu Ala Thr
    130                 135                 140

Leu Asn Asn Met Ser Glu Pro Tyr His Leu Ser Ile Gly Gln Val Leu
145                 150                 155                 160

Lys Ile Ala Asn Asn Ile Pro Asp Ser Asn Met Ile Pro Thr Gln Thr
                165                 170                 175

Ile Asn Glu Ser Glu Val Thr Gln Asn Thr Val Asn Glu Thr Trp Asn
            180                 185                 190

Ala Asn Lys Pro Thr Asn Glu Gln Met Lys Pro Val Ala Thr Pro Thr
        195                 200                 205

His Ser Thr Met Pro Ile Asn Lys Thr Pro Pro Ala Thr Ser Asn Ile
    210                 215                 220

Ala Trp Ile Trp Pro Thr Asn Gly Lys Ile Ile Gln Gly Phe Ser Ser
225                 230                 235                 240

Ala Asp Gly Gly Asn Lys Gly Ile Asp Ile Ser Gly Ser Arg Gly Gln
                245                 250                 255

Ala Val Asn Ala Ala Ala Ala Gly Arg Val Val Tyr Ala Gly Asp Ala
            260                 265                 270

Leu Arg Gly Tyr Gly Asn Leu Ile Ile Ile Lys His Asn Asp Ser Tyr
        275                 280                 285

Leu Ser Ala Tyr Ala His Asn Glu Ser Ile Leu Val Lys Asp Gln Gln
    290                 295                 300

Glu Val Lys Ala Gly Gln Gln Ile Ala Lys Met Gly Ser Ser Gly Thr
305                 310                 315                 320

Asn Thr Ile Lys Leu His Phe Glu Ile Arg Tyr Lys Gly Gln Ser Val
                325                 330                 335

Asp Pro Met Arg Tyr Leu Pro Lys Asn
            340                 345
```